United States Patent
Imanishi et al.

(10) Patent No.: US 7,615,619 B2
(45) Date of Patent: Nov. 10, 2009

(54) NUCLEOSIDE ANALOGUES AND OLIGONUCLEOTIDE DERIVATIVE COMPRISING NUCLEOTIDE ANALOGUE THEREOF

(75) Inventors: Takeshi Imanishi, Nara (JP); Satoshi Obika, Osaka (JP)

(73) Assignee: Takeshi Imanishi, Nara (JP)

( * ) Notice: Subject to any disclaimer, the term of this patent is extended or adjusted under 35 U.S.C. 154(b) by 223 days.

(21) Appl. No.: 10/504,165

(22) PCT Filed: Feb. 13, 2003

(86) PCT No.: PCT/JP03/01485

§ 371 (c)(1),
(2), (4) Date: May 23, 2005

(87) PCT Pub. No.: WO03/068795

PCT Pub. Date: Aug. 21, 2003

(65) Prior Publication Data

US 2006/0166908 A1 Jul. 27, 2006

(30) Foreign Application Priority Data

Feb. 13, 2002 (JP) ............................. 2002-035706

(51) Int. Cl.
C07H 21/00 (2006.01)
C07H 19/06 (2006.01)
C07H 19/10 (2006.01)
C07H 19/16 (2006.01)
C07H 19/20 (2006.01)

(52) U.S. Cl. .................... 536/23.1; 536/24.5; 536/26.7; 536/26.8; 536/27.1

(58) Field of Classification Search ................ None
See application file for complete search history.

(56) References Cited

U.S. PATENT DOCUMENTS

| | | | |
|---|---|---|---|
| 6,268,490 B1 * | 7/2001 | Imanishi et al. ............. 536/23.1 |
| 6,670,461 B1 | 12/2003 | Wengel et al. |
| 6,770,748 B2 * | 8/2004 | Imanishi et al. ............. 536/23.1 |
| 6,794,499 B2 | 9/2004 | Wengel et al. |
| 7,034,133 B2 | 4/2006 | Wengel et al. |
| 7,053,199 B2 * | 5/2006 | Imanishi et al. ............. 536/23.1 |

FOREIGN PATENT DOCUMENTS

EP 1 013 661 A 6/2000
EP 1013661 A1 6/2000

OTHER PUBLICATIONS

Burgers, Peter M.J. et al "Diastereomers of 5'-O-Adenosyl 3'-O-Uridyl Phosphorothioate: Chemical Synthesis and Enzymatic Properties" Biochemistry, (1979) vol. 18, No. 4, pp. 592-596.

Miller, Paul S. et al "Use of methylphosphonic dichloride for the synthesis of oligonucleoside methylphosphonates" Nucleic Acids Research (1983) vol. 11, No. 15, pp. 5189-5204.

Nielsen, Peter E. et al "Sequence-Selective Recognition of SNA by Strand Displacement with a Thymine-Substituted Polyamide" Science (1991) vol. 254, pp. 1497-1500.

Vandenriessche, Frank et al "Synthesis, Enzymatic Stability and Base-pairing Properties of Oligothymidylates Containing Thymidine Dimers with Different N-Substituted Guanidine Linkages" J. Chem. Soc. Perkin Trans. 1 (1993) pp. 1567-1575.

A. Koshikin et al., "LNA (Locked Nucleic Acids): Synthesis of the Adenine, Cystosine, Guanine, 5- Methylcytosine, Thymine and Uracil Bicyclonucleoside Monomers, Oligomerisation, and the Unprecedented Nucleic Acid Recognition", Tertrahedron, vol. 54., pp. 3607-3630, (1998), XP002094304.

Anne Lauritsen et al., "Oligodeoxynucleotides containing amide-linked LNA-type dinucleotides: synthesis and high-affinity nucleic acid hybridization", Chemical Communications, vol. 5, pp. 530-531, (2002), XP002469349 —.

Satoshi Obika et al., "Synthesis and Properties of 5'-amino-2'-BNA modified oligonucleotides with P3' .fwdarw.N5' phosphoramidate linkages", Nucleic Acids Research Supplement No. 2, vol. 2, pp. 25-26, (2002), XP008088731.

* cited by examiner

Primary Examiner—Lawrence E Crane
(74) Attorney, Agent, or Firm—Browdy and Neimark, P.L.L.C.

(57) ABSTRACT

A nucleotide analogue compound represented by formula (1) and salts thereof. In formula (1), A represents a direct bond, $C_{1-4}$ alkylene, etc.; B represents an optionally substituted aromatic heterocyclic groups; and $R_1$, $R_2$, $R_3$ and $R_4$ each represents hydrogen, an amino-protecting group, a hydroxyl-protecting group, a phosphate group, or —$P(R_7)R_8$, wherein $R_7$ and $R_8$ each represents hydroxyl, protected hydroxyl, mercapto, protected mercapto, etc. The compounds are useful as nucleotide analogues for producing oligonucleotide analogues useful in an antisense method and for producing intermediates thereof.

34 Claims, 1 Drawing Sheet

NUCLEOSIDE ANALOGUES AND OLIGONUCLEOTIDE DERIVATIVE COMPRISING NUCLEOTIDE ANALOGUE THEREOF

CROSS-REFERENCE TO RELATED APPLICATION

The application is a 35 U.S.C. 371 of PCT/JP03/01485, filed Feb. 13, 2003.

TECHNICAL FIELD

This invention relates to oligonucleotide analogues which have stable and excellent antisense or antigene activity, or have excellent activity as drugs for detection of particular genes or primers for initiation of amplification of particular genes, and which are useful as materials for various physiologically active or bioactive substances and pharmaceuticals, as functional materials for RNAi and decoy double-stranded oligonucleotides, as functional materials for DNA chips and molecular beacons targeting single-stranded nucleic acids such as cDNA, as functional materials for uses in various antisense methods (including ribozymes and DNAzymes) or antigene methods, and as materials for high sensitivity analysis of in vivo trace components by combination with fluorescent or luminescent substances. The invention also relates to nucleoside analogues, which are intermediates for production of the oligonucleotide analogues.

BACKGROUND ART

In 1978, it was reported for the first time that antisense molecules inhibited infection by influenza virus. Since then, reports have been issued that antisense molecules also inhibited oncogene expression and AIDS infection. Since antisense oligonucleotides specifically control the expression of undesirable genes, they have become one of the most promising fields as medicines in recent years.

The antisense method is based on the concept of controlling a series of information flow steps of the so-called central dogma, DNA→mRNA→protein, by use of an antisense oligonucleotide.

When a natural type oligonucleotide was applied as an antisense molecule to this method, however, problems arose such that it underwent hydrolysis by enzymes present in vivo, and its cell membrane permeation was not high. To resolve these problems, numerous nucleic acid derivatives have been synthesized, and have been extensively studied. For example, phosphorothioates having an oxygen atom on a phosphorus atom substituted by a sulfur atom, and methylphosphonates having an oxygen atom on a phosphorus atom substituted by a methyl group were synthesized. Recently, the derivatives having the phosphorus atom also substituted by a carbon atom, and molecules having ribose converted to an acyclic skeleton have also been synthesized (F. Eckstein et al., Biochem., 18, 592 (1979), P. S. Miller et al., Nucleic Acids Res., 11, 5189 (1983), P. Herdewijn et al., J. Chem. Soc. Perkin Trans. 1, 1567 (1993), P. E. Nielsen et al., Science, 254, 1497 (1991)).

However, none of these derivatives are fully satisfactory in in vivo stability, ease of synthesis of oligonucleotides, and so on.

In the light of the above-described conventional technologies, provision is desired of nucleotide analogues which have high cell membrane permeation under in vivo conditions, which are minimally hydrolyzed with enzymes, whose synthesis is easy, and which are useful for the antisense method, the antigene method, RNAi, and the decoy method.

DISCLOSURE OF THE INVENTION

We, the inventors of the present invention, designed nucleic acid derivatives with a modified sugar portion of nucleic acid, which may be useful as materials for various physiologically active or bioactive substances and pharmaceuticals, as functional materials for RNAi (Nature, Vol. 411, 494-498, 2001) and decoy double-stranded oligonucleotides, as functional materials for DNA chips and molecular beacons targeting single-stranded nucleic acids such as cDNA, as functional materials for uses in various antisense methods (including ribozymes and DNAzymes) or antigene methods, and as materials for high sensitivity analysis of in vivo trace components by combination with fluorescent or luminescent substances. We synthesized these nucleic acid derivative and confirmed their usefulness.

MODES FOR CARRYING OUT THE INVENTION

Figure 1:
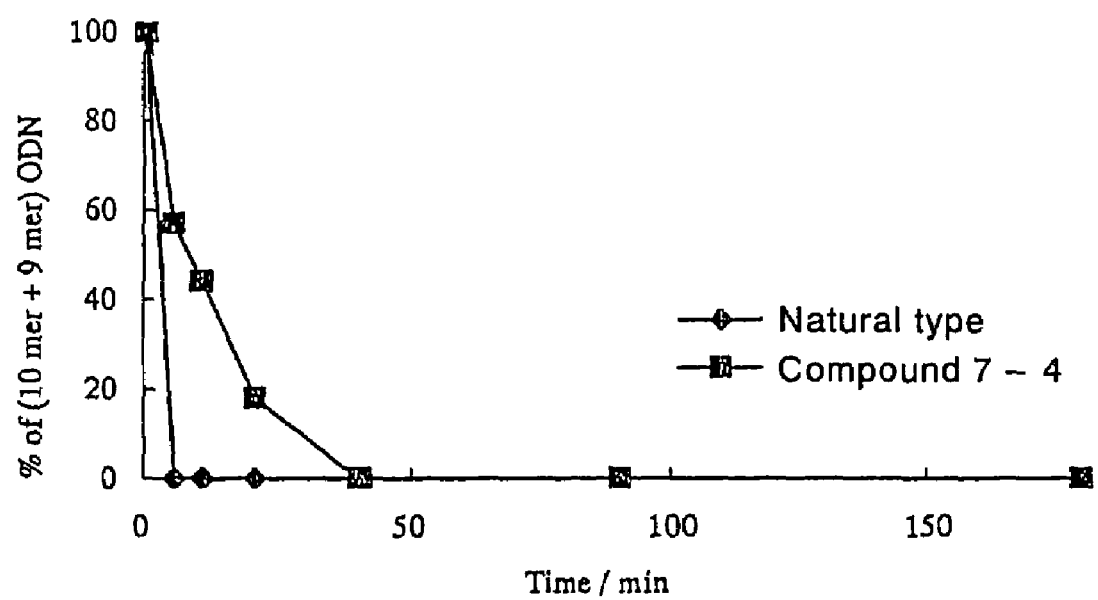
FIG. 1 is a graph showing changes with time in the ultra-violet absorption (260 nm) of a natural type oligonucleotide when degraded by an exonuclease, as a plot of % of (10mer+9mer) ODN versus time (min).

Nucleoside analogues of the present invention are compounds of the following general formula (1) and their salts:

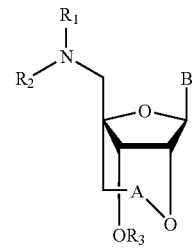

(1)

where A represents a direct bond, an alkylene group having 1 to 4 carbon atoms, —O—$(CH_2)_m$— (where the oxygen atom is linked to the methylene group at the 4'-position; m denotes an integer of 1 to 3), or —$N(R_4)$—$(CH_2)_n$— (where the nitrogen atom is linked to the methylene group at the 4'-position; n denotes an integer of 1 to 3), B represents an aromatic heterocyclic group or an aromatic hydrocarbon ring group which may have a substituent, and $R_1$, $R_2$, $R_3$ and $R_4$ are the same or different, and each represent a hydrogen atom, a protective group for a hydroxyl group for synthesis of nucleic acid, an alkyl group, an alkenyl group, a cycloalkyl group, an aralkyl group, an aryl group, an acyl group, a silyl group, a phosphate group, a phosphate group protected with a protective group for synthesis of nucleic acid, or —$P(R_7)R_8$ [where $R_7$ and $R_8$ are the same or different, and each represent a hydroxyl group, a hydroxyl group protected with a protective group for synthesis of nucleic acid, a mercapto group, a mercapto group protected with a protective group for synthesis of nucleic acid, an amino group, an alkoxy group having 1 to 5 carbon atoms, an alkylthio group having 1 to 5 carbon atoms, a cyanoalkoxy group having 1 to 6 carbon atoms, or an amino group substituted by an alkyl group having 1 to 5 carbon atoms].

Also, nucleoside analogues of the present invention are compounds of the following general formula (2) and their salts:

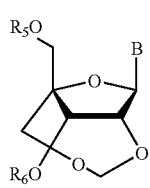

(2)

where B represents an aromatic heterocyclic group or an aromatic hydrocarbon ring group which may have a substituent, and $R_5$ and $R_6$ are the same or different, and each represent a hydrogen atom, a protective group for a hydroxyl group for synthesis of nucleic acid, an alkyl group, an alkenyl group, a cycloalkyl group, an aralkyl group, an aryl group, an acyl group, a silyl group, a phosphate group, a phosphate group protected with a protective group for synthesis of nucleic acid, or —$P(R_9)R_{10}$ [where $R_9$ and $R_{10}$ are the same or different, and each represent a hydroxyl group, a hydroxyl group protected with a protective group for synthesis of nucleic acid, a mercapto group, a mercapto group protected with a protective group for synthesis of nucleic acid, an amino group, an alkoxy group having 1 to 5 carbon atoms, an alkylthio group having 1 to 5 carbon atoms, a cyanoalkoxy group having 1 to 6 carbon atoms, or an amino group substituted by an alkyl group having 1 to 5 carbon atoms].

Nucleotide analogues of the present invention are oligonucleotide analogues containing one or more units having one or both of a structure represented by the following general formula (3) and a structure represented by the following general formula (4), or pharmacologically acceptable salts of the oligonucleotide analogues, provided that if the oligonucleotide analogues or salts thereof contain two or more units having one or both of these structures, B is the same or different among the structures.

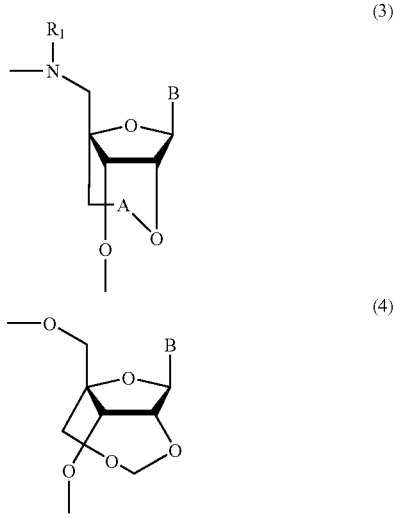

(3)

(4)

where A represents a direct bond, an alkylene group having 1 to 4 carbon atoms, —O—$(CH_2)_m$— (where the oxygen atom is linked to the methylene group at the 4'-position; m denotes an integer of 1 to 3), or —$N(R_4)$—$(CH_2)_n$— (where the nitrogen atom is linked to the methylene group at the 4'-position; n denotes an integer of 1 to 3), B represents an aromatic heterocyclic group or an aromatic hydrocarbon ring group which may have a substituent, and $R_1$ and $R_4$ are the same or different, and each represent a hydrogen atom, a protective group for a hydroxyl group for synthesis of nucleic acid, an alkyl group, an alkenyl group, a cycloalkyl group, an aralkyl group, an aryl group, an acyl group, a silyl group, a phosphate group, a phosphate group protected with a protective group for synthesis of nucleic acid, or —$P(R_7)R_8$ [where $R_7$ and $R_8$ are the same or different, and each represent a hydroxyl group, a hydroxyl group protected with a protective group for synthesis of nucleic acid, a mercapto group, a mercapto group protected with a protective group for synthesis of nucleic acid, an amino group, an alkoxy group having 1 to 5 carbon atoms, an alkylthio group having 1 to 5 carbon atoms, a cyanoalkoxy group having 1 to 6 carbon atoms, or an amino group substituted by an alkyl group having 1 to 5 carbon atoms].

In the present invention, examples of the "alkylene group having 1 to 4 carbon atoms" as A in the general formula (1) or (3) are methylene, ethylene, trimethylene, and tetramethylene groups. Preferred is a methylene group.

As "—O—$(CH_2)_m$—" defining A in the general formula (1) or (3), that with m=1, namely —O—$CH_2$—, is preferred.

As "—$N(R_4)$—$(CH_2)_m$—" defining A in the general formula (1) or (3), that with n=1, namely —$N(R_4)$—$CH_2$—, is preferred. Preferred as $R_4$ is a hydrogen atom or a lower alkyl group.

As A in the general formula (1) or (3), a direct bond or —O—$CH_2$— is preferred.

In the general formulas (1) to (4), the aromatic heterocyclic group as B refers to a structure in which the carbon atom, the constituent atom of a hydrocarbon ring, has been replaced by one or more heteroatoms such as nitrogen atoms, sulfur atoms or oxygen atoms. This structure represents any of groups having 5- to 20-membered rings and showing aromaticity, including a single ring and condensed rings. Concretely, the aromatic heterocyclic group includes, for example, pyrimidine or purine nucleic acid bases, and pyrimidine or purine nucleic acid bases which may have one or more substituents selected from the a group to be described below. The pyrimidine or purine nucleic acid bases include bases generally known as constituent elements of nucleic acids (for example, guanine, adenine, cytosine, thymine and uracil), and all chemical structures that can act as, or can be used instead of, other nucleic acid component bases similar to these bases. Others are also included, such as thiophene, thianthrene, furan, pyran, isobenzofuran, chromene, xanthene, phenoxthine, pyrrole, imidazole, pyrazole, isothiazole, isoxazole, pyridazine, indolizine, indole, isoindole, isoquinoline, quinoline, naphthyridine, quinoxaline, quinazoline, pteridine, carbazole, phenanthridine, acridine, perimidine, phenazine, phenarsazine, phenothiazine, brazan, phenoxazine, pyrrolidine, pyrroline, imidazolidine, imidazoline, and pyrazolidine. Preferably, the aromatic heterocyclic groups are the pyrimidine or purine nucleic acid bases, and pyrimidine or purine nucleic acid bases which may have one or more substituents selected from the a group to be described below. Concretely, the preferred one is a purin-9-yl group, a 2-oxo-pyrimidin-1-yl group, or a purin-9-yl group or a 2-oxo-pyrimidin-1-yl group which has a substituent selected from the following a group:

α group: A hydroxyl group, a hydroxyl group protected with a protective group for synthesis of nucleic acid, an alkoxy group having 1 to 5 carbon atoms, a mercapto group, a mercapto group protected with a protective group for synthesis of nucleic acid, an alkylthio group having 1 to 5 carbon atoms, an amino group, an amino group protected with a protective group for synthesis of nucleic acid, an amino group substituted by an alkyl group having 1 to 5 carbon atoms, an alkyl group having 1 to 5 carbon atoms, and a halogen atom.

Preferred as the "purine nucleic acid base which may have a substituent" is a 6-aminopurin-9-yl (i.e. adeninyl) group, a 6-aminopurin-9-yl group having an amino group protected with a protective group for synthesis of nucleic acid, a 2,6- diaminopurin-9-yl group, a 2-amino-6-chloropurin-9-yl group, a 2-amino-6-chloropurin-9-yl group having an amino group protected with a protective group for synthesis of nucleic acid, a 2-amino-6-fluoropurin-9-yl group, a 2-amino-6-fluoropurin-9-yl group having an amino group protected with a protective group for synthesis of nucleic acid, a 2-amino-6-bromopurin-9-yl group, a 2-amino-6-bromopurin-9-yl group having an amino group protected with a protective group for synthesis of nucleic acid, a 2-amino-6-hydroxypurin-9-yl (i.e. guaninyl) group, a 2-amino-6-hydroxypurin-9-yl group having an amino group protected with a protective group for synthesis of nucleic acid, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-2-yl group, or a 6-mercaptopurin-9-yl group. More preferred is a 6-benzoylaminopurin-9-yl group, an adeninyl group, a 2-isobutyrylamino-6-hydroxypurin-9-yl group, or a guaninyl group.

Preferred as the "pyrimidine nucleic acid base which may have a substituent" is a 2-oxo-4-amino-1,2-dihydropyrimidin-1-yl (i.e. cytosinyl) group, a 2-oxo-4-amino-1,2-dihydropyrimidin-1-yl group having an amino group protected with a protective group for synthesis of nucleic acid, a 2-oxo-4-amino-5-fluoro-1,2-dihydropyrimidin-1-yl group, a 2-oxo-4-amino-5-fluoro-1,2-dihydropyrimidin-1-yl group having an amino group protected with a protective group for synthesis of nucleic acid, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl (i.e. uracinyl) group, a 2-oxo-4-hydroxy-5-methyl-1,2-dihydropyrimidin-1-yl (i.e. thyminyl) group, or a 4-amino-5-methyl-2-oxo-1,2-dihydropyrimidin-1-yl (i.e. 5-methylcytosinyl) group. More preferred is a 2-oxo-4-benzoylamino-1,2-dihydropyrimidin-1-yl group, a cytosinyl group, a thyminyl group, a uracinyl group, a 2-oxo-4-benzoylamino-5-methyl-1,2-dihydropyrimidin-1-yl group, or a 5-methylcytosinyl group.

Of the "purine or pyrimidine nucleic acid bases which may have a substituent", still further preferred is a 6-aminopurin-9-yl (i.e. adeninyl) group, a 6-aminopurin-9-yl group having an amino group protected with a protective group for synthesis of nucleic acid, a 2,6-diaminopurin-9-yl group, a 2-amino-6-chloropurin-9-yl group, a 2-amino-6-chloropurin-9-yl group having an amino group protected with a protective group for synthesis of nucleic acid, a 2-amino-6-fluoropurin-9-yl group, a 2-amino-6-fluoropurin-9-yl group having an amino group protected with a protective group for synthesis of nucleic acid, a 2-amino-6-bromopurin-9-yl group, a 2-amino-6-bromopurin-9-yl group having an amino group protected with a protective group for synthesis of nucleic acid, a 2-amino-6-hydroxypurin-9-yl (i.e. guaninyl) group, a 2-amino-6-hydroxypurin-9-yl group having an amino group protected with a protective group for synthesis of nucleic acid, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, or a 6-mercaptopurin-9-yl group, a 2-oxo-4-amino-1,2-dihydropyrimidin-1-yl (i.e. cytosinyl) group, a 2-oxo-4-amino-1,2-dihydropyrimidin-1-yl group having an amino group protected with a protective group for synthesis of nucleic acid, a 2-oxo-4-amino-5-fluoro-1,2-dihydropyrimidin-1-yl group, a 2-oxo-4-amino-5-fluoro-1,2-dihydropyrimidin-1-yl group having an amino group protected with a protective group for synthesis of nucleic acid, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl (i.e. uracinyl) group, a 2-oxo-4-hydroxy-5-methyl-1,2-dihydropyrimidin-1-yl (i.e. thyminyl) group, or a 4-amino-5-methyl-2-oxo-1,2-dihydropyrimidin-1-yl (i.e. 5-methylcytosinyl) group, or a 4-amino-5-methyl-2-oxo-1,2-dihydropyrimidin-1-yl having an amino group protected with a protective group for synthesis of nucleic acid.

In the general formulas (1) to (4), the aromatic hydrocarbon ring group as B refers to a monovalent substituent remaining after removing one hydrogen atom from a hydrocarbon ring with 6 to 20 carbon atoms showing aromatic properties, and includes a single ring or condensed rings. Concretely, phenyl, indenyl, naphthyl, pentalenyl, azulenyl, heptalenyl, biphenylenyl, indacenyl, fluorenyl, phenanthryl, and anthryl, for example, are named. All structures that can be used instead as the base portion of the nucleic acid component in attaining the object of the present invention are also included as other examples. Moreover, the aromatic hydrocarbon ring may be substituted by one or more groups among a hydroxyl group, a hydroxyl group protected with a protective group for synthesis of nucleic acid, an amino group, an amino group protected with a protective group for.synthesis of nucleic acid, a halogen atom, a lower alkyl group, an alkoxy group, a carboxyl group, an aryloxy group, a nitro group, a trifluoromethyl group, and a phenyl group. Examples of such an optionally substituted aromatic hydrocarbon group are 4-hydroxyphenyl, 2-hydroxyphenyl, 4-aminophenyl, 2-aminophenyl, 2-methylphenyl, 2,6-dimethylphenyl, 2-chlorophenyl, 4-chlorophenyl, 2,4-dichlorophenyl, 2,5-dichlorophenyl, 2-bromophenyl, 4-methoxyphenyl, 4-chloro-2-nitrophenyl, 4-nitrophenyl, 2,4-dinitrophenyl, and biphenyl. Preferred examples of the optionally substituted aromatic hydrocarbon ring group are a phenyl group, and a phenyl group substituted by a hydroxyl group, a hydroxyl group protected with a protective group for synthesis of nucleic acid, an amino group, an amino group protected with a protective group for synthesis of nucleic acid, a lower alkoxy group, or a nitro group.

In the general formulas (1) to (3), the protective group in the "protective group for an amino group for synthesis of nucleic acid" and the "protective group for a hydroxyl group for synthesis of nucleic acid" as $R_1$, $R_2$, $R_3$, $R_4$, $R_5$ and $R_6$, and in the "hydroxyl group protected with a protective group for synthesis of nucleic acid" for $R_7$, $R_8$, $R_9$ and $R_{10}$ as well as for the a group is not limited, as long as the protective group can stably protect an amino group or a hydroxyl group during synthesis of nucleic acid. Concretely, the protective group refers to a protective group which is stable under acidic or neutral conditions and which can be cleft by a chemical method such as hydrogenolysis, hydrolysis, electrolysis or photolysis. Examples of such a protective group are "aliphatic acyl groups", including alkylcarbonyl groups such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl, and heneicosanoyl, carboxylated alkylcarbonyl groups such as succinoyl, glutaroyl and adipoyl, halogeno lower alkylcarbonyl groups such as chloroacetyl, dichloroacetyl, trichloroacetyl and trifluoroacetyl, lower alkoxy lower alkylcarbonyl groups such as methoxyacetyl, and unsaturated alkylcarbonyl groups such as (E)-2-methyl-2-butenoyl; "lower alkyl groups" such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, and 2-ethylbutyl; "lower alkenyl groups" such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl and 5-hexenyl; "aromatic acyl groups", including arylcarbonyl groups such as benzoyl, α-naphthoyl and β-naphthoyl, halogenoarylcarbonyl groups such as 2-bromobenzoyl and 4-chlorobenzoyl, lower alkylated arylcarbonyl groups such as 2,4,6-trimethylbenzoyl and 4-toluoyl, lower alkoxylated arylcarbonyl groups such as 4-anisoyl, carboxylated arylcarbonyl groups such as 2-carboxybenzoyl, 3-carboxybenzoyl and 4-carboxybenzoyl, nitrated arylcarbonyl groups such as 4-nitrobenzoyl and 2-nitrobenzoyl, lower alkoxycarbonylated arylcarbonyl groups such as 2-(methoxycarbonyl)benzoyl, and arylated arylcarbonyl groups such as 4-phenylbenzoyl; "tetrahydropyranyl or tetrahydrothiopyranyl groups" such as tetrahydropyran-2-yl, 3-bromotetrahydropyran-2-yl, 4-methoxytetrahydropyran-4-yl, tetrahydrothiopyran-4-yl and 4-methoxytetrahydrothiopyran-4-yl; "tetrahydrofuranyl or tetrahydrothiofuranyl groups" such as tetrahydrofuran-2-yl and tetrahydrothiofuran-2-yl; "silyl groups", including tri-lower alkylsilyl groups such as trimethylsilyl, triethylsilyl, isopropyldimethylsilyl, t-butyldimethylsilyl, methyldiisopropylsilyl, methyldi-t-butylsilyl, and triisopropylsilyl, and tri-lower alkylsilyl groups substituted by 1 or 2 aryl groups, such as diphenylmethylsilyl, diphenylbutylsilyl, diphenylisopropylsilyl and phenyldiisopropylsilyl; "lower alkoxymethyl groups" such as methoxymethyl, 1,1-dimethyl-1-methoxymethyl, ethoxymethyl, propoxymethyl, isopropoxymethyl, butoxymethyl and t-butoxymethyl; "lower alkoxylated lower alkoxymethyl groups" such as 2-methoxyethoxymethyl; "halogeno lower alkoxymethyl groups" such as 2,2,2-trichloroethoxymethyl and bis(2-chloroethoxy)methyl; "lower alkoxylated ethyl groups" such as 1-ethoxyethyl and 1-(isopropoxy)ethyl; "halogenated ethyl groups" such as 2,2,2-trichloroethyl; "methyl groups substituted by 1 to 3 aryl groups", such as benzyl, α-naphthylmethyl, β-naphthylmethyl, diphenylmethyl, triphenylmethyl, α-naphthyldiphenylmethyl, and 9-anthrylmethyl; "methyl groups substituted by 1 to 3 aryl groups, with the aryl ring being substituted by a lower alkyl, lower alkoxy, halogen or cyano group", such as 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 2-nitrobenzyl, 4-nitrobenzyl, 4-chlorobenzyl, 4-bromobenzyl, and 4-cyanobenzyl; "lower alkoxycarbonyl groups" such as methoxycarbonyl, ethoxycarbonyl, t-butoxycarbonyl, and isobutoxycarbonyl; "aryl groups substituted by a halogen atom, a lower alkoxy group or a nitro group", such as 4-chlorophenyl, 2-fluorophenyl, 4-methoxyphenyl, 4-nitrophenyl, and 2,4-dinitrophenyl; "lower alkoxycarbonyl groups substituted by halogen or a tri-lower alkylsilyl group", such as 2,2,2-trichloroethoxycarbonyl and 2-trimethylsilylethoxycarbonyl; "alkenyloxycarbonyl groups" such as vinyloxycarbonyl and aryloxycarbonyl; and "aralkyloxycarbonyl groups having an aryl ring optionally substituted by 1 or 2 lower alkoxy or nitro groups", such as benzyloxycarbonyl, 4-methoxybenzyloxycarbonyl, 3,4-dimethoxybenzyloxycarbonyl, 2-nitrobenzyloxycarbonyl, and 4-nitrobenzyloxycarbonyl. In the "protective group for a hydroxyl group for synthesis of nucleic acid" for $R_1$, $R_2$, $R_3$, $R_4$, $R_5$ and $R_6$, the preferred protective group is the "aliphatic acyl group," "aromatic acyl group," "methyl group substituted by 1 to 3 aryl groups", "methyl group substituted by 1 to 3 aryl groups, with the aryl ring being substituted by a lower alkyl, lower alkoxy, halogen or cyano group", or "silyl group", the more preferred protective group being an acetyl group, a benzoyl group, a benzyl group, a p-methoxybenzoyl group, a dimethoxytrityl group, a monomethoxytrityl group, or a tert-butyldiphenylsilyl group. Preferred as the protective group in the "hydroxyl group protected with a protective group for synthesis of nucleic acid" for $R_7$, $R_8$, $R_9$ and $R_{10}$ or the α-group is the "aliphatic acyl group," "aromatic acyl group," "methyl group substituted by 1 to 3 aryl groups", "aryl group substituted by a halogen atom, a lower alkoxy group or a nitro group", "lower alkyl group" or "lower alkenyl group", the more preferred protective group being a benzoyl group, a benzyl group, a 2-chlorophenyl group, a 4-chlorophenyl group or a 2-propenyl group.

In the general formulas (1) to (3), the "alkyl group" as $R_1$, $R_2$, $R_3$, $R_4$, $R_5$ and $R_6$ refers to a straight chain or branched chain alkyl group having 1 to 20 carbon atoms, including not only a straight chain or branched chain alkyl group having 1 to 6 carbon atoms (herein, also referred to as a lower alkyl group), such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, or 2-ethylbutyl, but also a straight chain or branched chain alkyl group having 7 to 20 carbon atoms, such as heptyl, octyl, nonyl or decyl. Preferred is the above-mentioned straight chain or branched chain alkyl group having 1 to 6 carbon atoms.

In the general formulas (1) to (3), the "alkenyl group" as $R_1$, $R_2$, $R_3$, $R_4$, $R_5$ and $R_6$ refers to a straight chain or branched chain alkenyl group having 2 to 20 carbon atoms, including not only a straight chain or branched chain alkenyl group having 2 to 6 carbon atoms (herein, also referred to as a lower alkenyl group), such as ethenyl, 1-propenyl, 2-propenyl, 1-methyl-2-propenyl, 1-methyl-1-propenyl, 2-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl or 5-hexenyl, but also geranyl or farnesyl. Preferred is the above-mentioned straight chain or branched chain alkenyl group having 2 to 6 carbon atoms.

In the general formulas (1) to (3), the "cycloalkyl group" as $R_1$, $R_2$, $R_3$, $R_4$, $R_5$ and $R_6$ refers to a cycloalkyl group having 3 to 10 carbon atoms, including, for example, cyclopropyl, cyclobutyl, cyclopentyl, cyclohexyl, cycloheptyl, cyclooctyl, norbornyl or adamantyl. Preferred is a cycloalkyl group having 3 to 8 carbon atoms, such as cyclopropyl, cyclobutyl, cyclopentyl, cyclohexyl, cycloheptyl or cyclooctyl. Also, the "cycloalkyl group" includes a heterocyclic group in which one or more methylene groups on the ring of the cycloalkyl group have been substituted by an oxygen atom, a sulfur atom or a nitrogen atom substituted by an alkyl group. An example of such a substituted heterocyclic group is a tetrahydropyranyl group.

In the general formulas (1) to (3), the "aryl group" as $R_1$, $R_2$, $R_3$, $R_4$, $R_5$ and $R_6$ refers to a monovalent substituent having 6 to 14 carbon atoms, which is obtained by removing one hydrogen atom from an aromatic hydrocarbon group. Its examples are phenyl, indenyl, naphthyl, phenanthrenyl, and anthracenyl. Its aryl ring may be substituted by one or more of groups, including a halogen atom, a lower alkyl group, a hydroxyl group, an alkoxy group, an aryloxy group, an amino group, a nitro group, a trifluoromethyl group, and a phenyl group. Examples of the optionally substituted aryl group are 2-methylphenyl, 2,6-dimethylphenyl, 2-chlorophenyl, 4-chlorophenyl, 2,4-dichlorophenyl, 2,5-dichlorophenyl, 2-bromophenyl, 4-methoxyphenyl, 4-chloro-2-nitrophenyl, 4-nitrophenyl, 2,4-dinitrophenyl, and biphenyl. Preferred examples thereof are a phenyl group, and a phenyl group substituted by a halogen atom, a lower alkoxy group, or a nitro group.

In the general formulas (1) to (3), the "aralkyl group" as $R_1$, $R_2$, $R_3$, $R_4$, $R_5$ and $R_6$ refers to an alkyl group with 1 to 6 carbon atoms substituted by an aryl group. Examples of such an aryl-substituted alkyl group are "methyl groups substituted by 1 to 3 aryl groups", such as benzyl, α-naphthylmethyl, β-naphthylmethyl, indenylmethyl, phenanthrenylmethyl, anthracenylmethyl, diphenylmethyl, triphenylmethyl, α-naphthyldiphenylmethyl, and 9-anthrylmethyl; "methyl groups substituted by 1 to 3 aryl groups, with the aryl ring being substituted by a lower alkyl, lower alkoxy, halogen or cyano group", such as 4-methylbenzyl, 2,4,6-trimethylbenzyl, 3,4,5-trimethylbenzyl, 4-methoxybenzyl, 4-methoxyphenyldiphenylmethyl, 4,4'-dimethoxytriphenylmethyl, 2-nitrobenzyl, 4-nitrobenzyl, 4-chlorobenzyl, 4-bromobenzyl, and 4-cyanobenzyl; and "alkyl groups with 3 to 6 carbon atoms substituted by an aryl group", such as 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylpentyl, 2-naphthylpentyl, 3-naphthylpentyl, 4-naphthylpentyl, 5-naphthylpentyl, and 6-naphthylpentyl. Preferred are the "methyl groups substituted by 1 to 3 aryl groups" and "methyl groups substituted by 1 to 3 aryl groups, with the aryl ring being substituted by a lower alkyl, lower alkoxy, halogen or cyano group". More preferred are 4-methoxyphenyldiphenylmethyl and 4,4'-dimethoxytriphenylmethyl.

Examples of the "acyl group" as $R_1$, $R_2$, $R_3$, $R_4$, $R_5$ and $R_6$ in the general formulas (1) to (3) are "aliphatic acyl groups", including alkylcarbonyl groups, such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, eicosanoyl, and heneicosanoyl, carboxylated alkylcarbonyl groups such as succinoyl, glutaroyl and adipoyl, halogeno lower alkylcarbonyl groups such as chloroacetyl, dichloroacetyl, trichloroacetyl and trifluoroacetyl, lower alkoxy lower alkylcarbonyl groups such as methoxyacetyl, and unsaturated alkylcarbonyl groups such as (E)-2-methyl-2-butenoyl; and "aromatic acyl groups", including arylcarbonyl groups, such as benzoyl, α-naphthoyl and β-naphthoyl, halogenoarylcarbonyl groups such as 2-bromobenzoyl and 4-chlorobenzoyl, lower alkylated arylcarbonyl groups such as 2,4,6-trimethylbenzoyl and 4-toluoyl, lower alkoxylated arylcarbonyl groups such as 4-anisoyl, carboxylated arylcarbonyl groups such as 2-carboxybenzoyl, 3-carboxybenzoyl and 4-carboxybenzoyl, nitrated arylcarbonyl groups such as 4-nitrobenzoyl and 2-nitrobenzoyl, lower alkoxycarbonylated arylcarbonyl groups such as 2-(methoxycarbonyl)benzoyl, and arylated arylcarbonyl groups such as 4-phenylbenzoyl. Preferred examples are formyl, acetyl, propionyl, butyryl, isobutyryl, pentanoyl, pivaloyl, and benzoyl groups.

Examples of the "silyl group" as $R_1$, $R_2$, $R_3$, $R_4$, $R_5$ and $R_6$ in the general formulas (1) to (3) are "tri-lower alkylsilyl groups" such as trimethylsilyl, triethylsilyl, isopropyldimethylsilyl, t-butyldimethylsilyl, methyldiisopropylsilyl, methyldi-t-butylsilyl, and triisopropylsilyl, and "tri-lower alkylsilyl groups substituted by 1 or 2 aryl groups", such as diphenylmethylsilyl, butyldiphenylbutylsilyl, diphenylisopropylsilyl and phenyldiisopropylsilyl. Preferred examples are trimethylsilyl, triethylsilyl, triisopropylsilyl, t-butyldimethylsilyl, and t-butyldiphenylsilyl. A more preferred example is trimethylsilyl.

In the general formulas (1) to (3), the protective group in the "phosphate group protected with a protective group for synthesis of nucleic acid" as $R_1$, $R_2$, $R_3$, $R_4$, $R_5$ and $R_6$ is not limited, as long as the protective group can stably protect a phosphate group during synthesis of nucleic acid. Concretely, the protective group refers to a protective group which is stable under acidic or neutral conditions and which can be cleft by a chemical method such as hydrogenolysis, hydrolysis, electrolysis or photolysis. Examples of such a protective group are "lower alkyl groups" such as methyl, ethyl, n-propyl, isopropyl, n-butyl, isobutyl, s-butyl, tert-butyl, n-pentyl, isopentyl, 2-methylbutyl, neopentyl, 1-ethylpropyl, n-hexyl, isohexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, and 2-ethylbutyl; "cyanated lower alkyl groups" such as 2-cyanoethyl, and 2-cyano-1,1-dimethylethyl; "ethyl groups substituted by a silyl group", such as 2-methyldiphenylsilylethyl, 2-trimethylsilylethyl and 2-triphenylsilylethyl; "halogenated lower alkyl groups" such as 2,2,2-trichloroethyl, 2,2,2-tribromoethyl, 2,2,2-trifluoroethyl and 2,2,2-trichloro-1,1-dimethylethyl; "lower alkenyl groups" such as ethenyl, 1-propenyl, 2-propenyl, 1-methyl-2-propenyl, 1-methyl-1-propenyl, 2-methyl-2-propenyl, 2-ethyl-2-propenyl, 1-butenyl, 2-butenyl, 1-methyl-2-butenyl, 1-methyl-1-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl and 5-hexenyl; "cycloalkyl groups" such as cyclopropyl, cyclobutyl, cyclopentyl, cyclohexyl, cycloheptyl, norbornyl or adamantyl; "cyanated lower alkenyl groups" such as 2-cyanobutenyl; "aralkyl groups" such as benzyl, α-naphthylmethyl, β-naphthylmethyl, indenylmethyl, phenanthrenylmethyl, anthracenylmethyl, diphenylmethyl, triphenylmethyl, 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl, 1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylpentyl, 2-naphthylpentyl, 3-naphthylpentyl, 4-naphthylpentyl, 5-naphthylpentyl, and 6-naphthylpentyl; "aralkyl groups having an aryl ring substituted by a nitro group or a halogen atom", such as 4-chlorobenzyl, 2-(4-nitrophenyl)ethyl, o-nitrobenzyl, 4-nitrobenzyl, 2,4-dinitrobenzyl, and 4-chloro-2-nitrobenzyl; "aryl groups" such as phenyl, indenyl, naphthyl, phenanthrenyl and anthracenyl; and "aryl groups substituted by a lower alkyl group, a halogen atom or a nitro group", such as 2-methylphenyl, 2,6-dimethylphenyl, 2-chlorophenyl, 4-chlorophenyl, 2,4-dichlorophenyl, 2,5-dichlorophenyl, 2-bromophenyl, 4-nitrophenyl, and 4-chloro-2-nitrophenyl. Preferred examples are the "lower alkyl groups", "lower alkyl groups substituted by a cyano group", "aralkyl groups", "aralkyl groups having an aryl ring substituted by a nitro group or a halogen atom", or "aryl groups substituted by a lower alkyl group, a halogen atom or a nitro group". A more preferred examples is a 2-cyanoethyl group, a 2,2,2-trichloroethyl group, a benzyl group, a 2-chlorophenyl group, or a 4-chlorophenyl group.

In the general formulas (1) to (3), the protective group in the "mercapto group protected with a protective group for synthesis of nucleic acid" as $R_7$, $R_8$, $R_9$ and $R_{10}$ as well as the a group is not limited, as long as the protective group can stably protect a mercapto group during synthesis of nucleic acid. Concretely, the protective group refers to a protective group which is stable under acidic or neutral conditions and which can be cleft by a chemical method such as hydrogenolysis, hydrolysis, electrolysis or photolysis. Examples of such a protective group are not only those named above as the protective group for a hydroxyl group, but also "disulfide-forming groups", including alkylthio groups such as methylthio, ethylthio and tert-butylthio, and arylthio groups such as benzylthio. Preferred examples are "aliphatic acyl groups" or "aromatic acyl groups". A more preferred example is a benzoyl group.

Examples of the "alkoxy groups having 1 to 5 carbon atoms" as $R_7$, $R_8$, $R_9$ and $R_{10}$ as well as the α group in the general formulas (1) to (3) are methoxy, ethoxy, n-propoxy, isopropoxy, n-butoxy, isobutoxy, s-butoxy, tert-butoxy, and n-pentoxy. A preferred example is a methoxy or ethoxy group.

Examples of the "alkoxythio groups having 1 to 5 carbon atoms" as $R_7$, $R_8$, $R_9$ and $R_{10}$ as well as the α group in the general formulas (1) to (3) are methylthio, ethylthio, propylthio, isopropylthio, butylthio, isobutylthio, s-butylthio, tert-butylthio, and n-pentylthio. A preferred example is a methylthio or ethylthio group.

The "cyanoalkoxy group having 1 to 6 carbon atoms" as $R_7$, $R_8$, $R_9$ and $R_{10}$ in the general formulas (1) to (3) refers to the above-mentioned "alkoxy group having 1 to 5 carbon atoms" which has been substituted by a cyano group. Examples of such a cyano-substituted alkoxy group are cyanomethoxy, 2-cyanoethoxy, 3-cyanopropoxy, 4-cyanobutoxy, 3-cyano-2-methylpropoxy, and 1-cyanomethyl-1,1-dimethylmethoxy. A preferred example is a 2-cyanoethoxy group.

Examples of the "amino group substituted by an alkyl group having 1 to 5 carbon atoms" as $R_7$, $R_8$, $R_9$ and $R_{10}$ as well as the a group in the general formulas (1) to (3) are methylamino, ethylamino, propylamino, isopropylamino, butylamino, isobutylamino, s-butylamino, tert-butylamino, dimethylamino, diethylamino, dipropylamino, diisopropylamino, dibutylamino, diisobutylamino, di(s-butyl)amino, and di(tert-butyl)amino. A preferred example is a methylamino, ethylamino, dimethylamino, diethylamino or diisopropylamino group.

Examples of the "alkyl group having 1 to 5 carbon atoms" as the a group are methyl, ethyl, propyl, isopropyl, isopropyl, butyl, isobutyl, s-butyl, tert-butyl, and n-pentyl. A preferred example is a methyl or ethyl group.

As the "halogen atom" for the α group, a fluorine atom, a chlorine atom, a bromine atom or an iodine atom, for example, can be named. A preferred example thereof is a fluorine atom or a chlorine atom. The "phosphoroamidite group" refers to a group represented by the formula —P($OR_{3a}$)($NR_{3b}$) (where $R_{3a}$ represents an alkyl group having 1 or more carbon atoms or a cyanoalkyl group having 1 to 7 carbon atoms, and $R_{3b}$ represents an alkyl group having 1 to 6 carbon atoms). Its preferred example is a group represented by the formula —P($OC_2H_4CN$)(N(iPr)$_2$) or a group represented by the formula —P($OCH_3$)(N(iPr)$_2$).

The protective group in the "amino group protected with a protective group for synthesis of nucleic acid" as the a group is not limited, as long as the protective group can stably protect an amino group during synthesis of nucleic acid. Concretely, the protective group refers to a protective group which is stable under acidic or neutral conditions and which can be cleft by a chemical method such as hydrogenolysis, hydrolysis, electrolysis or photolysis. Examples of such a protective group are "aliphatic acyl groups", including alkylcarbonyl groups, such as formyl, acetyl, propionyl, butyryl, isobutyryl, pentanoyl, pivaloyl, valeryl, isovaleryl, octanoyl, nonanoyl, decanoyl, 3-methylnonanoyl, 8-methylnonanoyl, 3-ethyloctanoyl, 3,7-dimethyloctanoyl, undecanoyl, dodecanoyl, tridecanoyl, tetradecanoyl, pentadecanoyl, hexadecanoyl, 1-methylpentadecanoyl, 14-methylpentadecanoyl, 13,13-dimethyltetradecanoyl, heptadecanoyl, 15-methylhexadecanoyl, octadecanoyl, 1-methylheptadecanoyl, nonadecanoyl, nonadecanoyl, eicosanoyl, and heneicosanoyl, carboxylated alkylcarbonyl groups such as succinoyl, glutaroyl and adipoyl, halogeno lower alkylcarbonyl groups such as chloroacetyl, dichloroacetyl, trichloroacetyl and trifluoroacetyl, lower alkoxy lower alkylcarbonyl groups such as methoxyacetyl, and unsaturated alkylcarbonyl groups such as (E)-2-methyl-2-butenoyl; "aromatic acyl groups", including arylcarbonyl groups, such as benzoyl, α-naphthoyl and β-naphthoyl, halogenoarylcarbonyl groups such as 2-bromobenzoyl and 4-chlorobenzoyl, lower alkylated arylcarbonyl groups such as 2,4,6-trimethylbenzoyl and 4-toluoyl, lower alkoxylated arylcarbonyl groups such as 4-anisoyl, carboxylated arylcarbonyl groups such as 2-carboxybenzoyl, 3-carboxybenzoyl and 4-carboxybenzoyl, nitrated arylcarbonyl groups such as 4-nitrobenzoyl and 2-nitrobenzoyl, lower alkoxycarbonylated arylcarbonyl groups such as 2-(methoxycarbonyl)benzoyl, and arylated arylcarbonyl groups such as 4-phenylbenzoyl; "lower alkoxycarbonyl groups" such as methoxycarbonyl, ethoxycarbonyl, t-butoxycarbonyl, and isobutoxycarbonyl; "lower alkoxycarbonyl groups substituted by halogen or a tri-lower alkylsilyl group", such as 2,2,2-trichloroethoxycarbonyl and 2-trimethylsilylethoxycarbonyl; "alkenyloxycarbonyl groups" such as vinyloxycarbonyl and aryloxycarbonyl; and "aralkyloxycarbonyl groups having an aryl ring optionally substituted by one or two lower alkoxy or nitro groups", such as benzyloxycarbonyl, 4-methoxybenzyloxycarbonyl, 2-nitrobenzyloxycarbonyl, and 4-nitrobenzyloxycarbonyl. Preferred examples of the protective group are the "aliphatic acyl groups" or "aromatic acyl groups", and a more preferred example is a benzoyl group.

The "nucleoside analogues" refers to non-natural type nucleosides among "nucleosides" comprising purine or pyrimidine bases and sugars linked together, and also those comprising aromatic heterocyclic rings or aromatic hydrocarbon rings, which are other than purine and pyrimidine and which can be used instead of purine and pyrimidine, and sugars linked thereto.

The "oligonucleotide analogues" refer to non-natural type derivatives of "oligonucleotides" consisting of 2 to 50 identical or different "nucleosides" or "nucleoside analogues" linked together by phosphodiester bonds. Preferred examples of such analogues are sugar derivatives with the sugar portion modified; thioate derivatives with the phosphodiester portion thioated; ester compounds with the terminal phosphate portion esterified; and amide compounds with the amino group on the purine base being amidated. More preferred examples are the sugar derivatives with the sugar portion modified.

The "salts thereof" refer to salts of the compounds (1) and (2) of the present invention, because these compounds can be converted into salts. Preferred examples of such salts are metal salts including alkali metal salts such as sodium salts, potassium salts and lithium salts, alkaline earth metal salts such as calcium salts and magnesium salts, and aluminum salts, iron salts, zinc salts, copper salts, nickel salts and cobalt salts; amine salts, including inorganic salts such as ammonium salts, and organic salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, and tris(hydroxymethyl)aminomethane salts; inorganic acid salts, including halogenated hydroacid salts such as hydrofluorides, hydrochlorides, hydrobromides and hydriodides, nitrates, perchlorates, sulfates and phosphates; organic acid salts, including lower alkane sulfonic acid salts such as methanesulfonates, trifluoromethanesulfonates, and ethanesulfonates, aryl sulfonic acid salts such as benzenesulfonates and p-toluenesulfonates, acetates, malates, fumarates, succinates, citrates, tartarates, oxalates, and maleates; and amino acids, such as glycine salts, lysine salts, arginine salts, ornithine salts, glutamates and aspartates.

The "pharmacologically acceptable salts thereof" refer to salts of the oligonucleotide analogues of the present invention, because these analogues can be converted into salts. Preferred examples of such salts are metal salts including alkali metal salts such as sodium salts, potassium salts and lithium salts, alkaline earth metal salts such as calcium salts and magnesium salts, and aluminum salts, iron salts, zinc salts, copper salts, nickel salts and cobalt salts; amine salts, including inorganic salts such as ammonium salts, and organic salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, and tris(hydroxymethyl)aminomethane salts; inorganic acid salts, including halogenated hydroacid salts such as hydrofluorides, hydrochlorides, hydrobromides and hydriodides, nitrates, perchlorates, sulfates and phosphates; organic acid salts, including lower alkane sulfonic acid salts such as methanesulfonates, trifluoromethanesulfonates, and ethanesulfonates, aryl sulfonic acid salts such as benzenesulfonates and p-toluenesulfonates, acetates, malates, fumarates, succinates, citrates, tartarates, oxalates, and maleates; and amino acids, such as glycine salts, lysine salts, arginine salts, ornithine salts, glutamates and aspartates.

Of the compounds (1) and salts thereof according to the present invention, the preferred compounds are, for example, as follows:

(1) Compounds and salts thereof, wherein $R_1$ and $R_2$ are the same or different and each represent a hydrogen atom, an aliphatic acyl group, an aromatic acyl group, a methyl group substituted by 1 to 3 aryl groups, a methyl group substituted by 1 to 3 aryl groups, with the aryl rings being substituted by a lower alkyl, lower alkoxy, halogen or cyano group, or a silyl group.

(2) Compounds and salts thereof, wherein $R_1$ and $R_2$ are the same or different and each represent a hydrogen atom, an acetyl group, a benzoyl group, a benzyl group, a p-methoxybenzyl group, a dimethoxytrityl group, a monomethoxytrityl group, or a tert-butyldiphenylsilyl group.

(3) Compounds and salts thereof, wherein $R_3$ represents a hydrogen atom, an aliphatic acyl group, an aromatic acyl group, a methyl group substituted by 1 to 3 aryl groups, a methyl group substituted by 1 to 3 aryl groups, with the aryl rings being substituted by a lower alkyl, lower alkoxy, halogen or cyano group, a silyl group, a phosphoroamidite group, a phosphonyl group, a phosphate group, or a phosphate group protected with a protective group for synthesis of nucleic acid.

(4) Compounds and salts thereof, wherein $R_3$ represents a hydrogen atom, an acetyl group, a benzoyl group, a benzyl group, a p-methoxybenzyl group, a tert-butyldiphenylsilyl group, —P(OC$_2$H$_4$CN)(N(iPr)$_2$), —P(OCH$_3$)(N(iPr)$_2$), a phosphonyl group, or a 2-chlorophenyl- or 4-chlorophenylphosphate group.

(5) Compounds and salts thereof, wherein A represents a direct bond or —O—(CH$_2$)— (where the oxygen atom is linked to the methylene group at the 4'-position).

(6) Compounds and salts thereof, wherein B represents a 6-aminopurin-9-yl (i.e. adeninyl) group, a 6-aminopurin-9-yl group having an amino group protected with a protective group for synthesis of nucleic acid, a 2,6-diaminopurin-9-yl group, a 2-amino-6-chloropurin-9-yl group, a 2-amino-6-chloropurin-9-yl group having an amino group protected with a protective group for synthesis of nucleic acid, a 2-amino-6-fluoropurin-9-yl group, a 2-amino-6-fluoropurin-9-yl group having an amino group protected with a protective group for synthesis of nucleic acid, a 2-amino-6-bromopurin-9-yl group, a 2-amino-6-bromopurin-9-yl group having an amino group protected with a protective group for synthesis of nucleic acid, a 2-amino-6-hydroxypurin-9-yl (i.e. guaninyl) group, a 2-amino-6-hydroxypurin-9-yl group having an amino group protected with a protective group for synthesis of nucleic acid, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl (i.e. cytosinyl) group, a 2-oxo-4-amino-1,2-dihydropyrimidin-1-yl group having an amino group protected with a protective group for synthesis of nucleic acid, a 2-oxo-4-amino-5-fluoro-1,2-dihydropyrimidin-1-yl group, a 2-oxo-4-amino-5-fluoro-1,2-dihydropyrimidin-1-yl group having an amino group protected with a protective group for synthesis of nucleic acid, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl (i.e. uracinyl) group, a 2-oxo-4-hydroxy-5-methyl-1,2-dihydropyrimidin-1-yl (i.e. thyminyl) group, a 4-amino-5-methyl-2-oxo-1,2-dihydropyrimidin-1-yl (i.e. 5-methylcytosinyl) group, or a 4-amino-5-methyl-2-oxo-1,2-dihydropyrimidin-1-yl group having an amino group protected with a protective group for synthesis of nucleic acid.

(7) Compounds and salts thereof, wherein B represents a benzoylaminopurin-9-yl, adenyl, 2-isobutyrylamino-6-hydroxypurin-9-yl, guaninyl, 2-oxo-4-benzoylamino-1,2-dihydropyrimidin-1-yl, cytosinyl, 2-oxo-5-methyl-4-benzoylamino-1,2-dihydropyrimidin-1-yl, 5-methylcytosinyl, uracinyl or thyminyl group.

In connection with the above compounds (1) to (2), (3) to (4) or (6) to (7), the greater their number is, the more preferred these compounds become. Also preferred are compounds and salts thereof obtained by arbitrarily selecting, in the general formula (1), $R_1$ and $R_2$ from the compounds and salts (1) to (2), $R_3$ from the compounds and salts (3) to (4), A from the compounds and salts (5), and B from the compounds and salts (6) to (7), or by arbitrarily combining these selections. Particularly preferred combinations are (2)-(3)-(5)-(6), (2)-(3)-(5)-(7), (2)-(4)-(5)-(6) and (2)-(4)-(5)-(7).

Of the compounds (2) and salts thereof according to the present invention, the preferred compounds are, for example, as follows:

(8) Compounds and salts thereof, wherein $R_5$ is the same or different and represents a hydrogen atom, an aliphatic acyl group, an aromatic acyl group, a methyl group substituted by 1 to 3 aryl groups, a methyl group substituted by 1 to 3 aryl groups, with the aryl rings being substituted by a lower alkyl, lower alkoxy, halogen or cyano group, or a silyl group.

(9) Compounds and salts thereof, wherein $R_5$ is the same or different and represents a hydrogen atom, an acetyl group, a benzoyl group, a benzyl group, a p-methoxybenzyl group, a dimethoxytrityl group, a monomethoxytrityl group, or a tert-butyldiphenylsilyl group.

(10) Compounds and salts thereof, wherein $R_6$ represents a hydrogen atom, an aliphatic acyl group, an aromatic acyl group, a methyl group substituted by 1 to 3 aryl groups, a methyl group substituted by 1 to 3 aryl groups, with the aryl rings being substituted by a lower alkyl, lower alkoxy, halogen or cyano group, a silyl group, a phosphoroamidite group, a phosphonyl group, a phosphate group, or a phosphate group protected with a protective group for synthesis of nucleic acid.

(11) Compounds and salts thereof, wherein $R_6$ represents a hydrogen atom, an acetyl group, a benzoyl group, a benzyl group, a p-methoxybenzyl group, a tert-butyldiphenylsilyl group, —P(OC$_2$H$_4$CN)(N(iPr)$_2$), —P(OCH$_3$)(N(iPr)$_2$), a phosphonyl group, or a 2-chlorophenyl- or 4-chlorophenylphosphate group.

(12) Compounds and salts thereof, wherein B represents a 6-aminopurin-9-yl (i.e. adeninyl) group, a 6-aminopurin-9-yl group having an amino group protected with a protective group for synthesis of nucleic acid, a 2,6-diaminopurin-9-yl group, a 2-amino-6-chloropurin-9-yl group, a 2-amino-6-chloropurin-9-yl group having an amino group protected with a protective group for synthesis of nucleic acid, a 2-amino-6-fluoropurin-9-yl group, a 2-amino-6-fluoropurin-9-yl group having an amino group protected with a protective group for synthesis of nucleic acid, a 2-amino-6-bromopurin-9-yl group, a 2-amino-6-bromopurin-9-yl group having an amino group protected with a protective group for synthesis of nucleic acid, a 2-amino-6-hydroxypurin-9-yl (i.e. guaninyl) group, a 2-amino-6-hydroxypurin-9-yl group having an amino group protected with a protective group for synthesis of nucleic acid, a 6-amino-2-methoxypurin-9-yl group, a 6-amino-2-chloropurin-9-yl group, a 6-amino-2-fluoropurin-9-yl group, a 2,6.-dimethoxypurin-9-yl group, a 2,6-dichloropurin-9-yl group, a 6-mercaptopurin-9-yl group, a 2-oxo-4-amino-1,2-dihydropyrimidin-1-yl (i.e. cytosinyl) group, a 2-oxo-4-amino-1,2-dihydropyrimidin-1-yl group having an amino group protected with a protective group for synthesis of nucleic acid, a 2-oxo-4-amino-5-fluoro-1,2-dihydropyrimidin-1-yl group, a 2-oxo-4-amino-5-fluoro-1,2-dihydropyrimidin-1-yl group having an amino group protected with a protective group for synthesis of nucleic acid, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl (i.e. uracinyl) group, a 2-oxo-4-hydroxy-5-methyl-1,2-dihydropyrimidin-1-yl (i.e. thyminyl) group, a 4-amino-5-methyl-2-oxo-1,2-dihydropyrimidin-1-yl (i.e. 5-methylcytosinyl) group, or a 4-amino-5-methyl-2-oxo-1,2-dihydropyrimidin-1-yl group having an amino group protected with a protective group for synthesis of nucleic acid.

(13) Compounds and salts thereof, wherein B represents a benzoylaminopurin-9-yl, adenyl, 2-isobutyrylamino-6-hydroxypurin-9-yl, guaninyl, 2-oxo-4-benzoylamino-1,2-dihydropyrimidin-1-yl, cytosinyl, 2-oxo-5-methyl-4-benzoylamino-1,2-dihydropyrimidin-1-yl, 5-methylcytosinyl, uracinyl or thyminyl group.

In connection with the above compounds (8) to (9), (10) to (11) or (12) to (13), the greater their number is, the more preferred these compounds become. Also preferred are compounds and salts thereof obtained by arbitrarily selecting, in the general formula (2), $R_1$ and $R_2$ from the compounds and salts (8) to (9), $R_3$ from the compounds and salts (10) to (11), and B from the compounds and salts (12) to (13), or by arbitrarily combining these selections. Particularly preferred combinations are (9)-(10)-(12), (9)-(10)-(13), (9)-(11)-(12) and (9)-(11)-(13).

Of the compounds of the general formula (1) and salts thereof, particularly preferred are the compounds and salts thereof selected from the following groups:

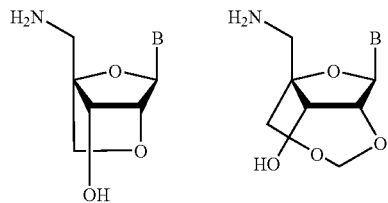

In the structural formulas of the above groups, B is as defined earlier.

Of the compounds of the general formula (2) and salts thereof, particularly preferred are the compounds and salts thereof selected from the following group:

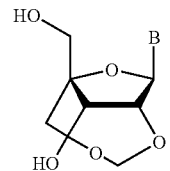

In the structural formula of the above group, B is as defined earlier.

Of oligonucleotide analogues containing one or more units having one or both of the structures represented by the general formulas (3) and (4) according to the present invention, or pharmacologically acceptable salts thereof, the preferred ones, if they contain the structure of the general formula (3), are, for example,

(14) Oligonucleotide analogues and pharmacologically acceptable salts thereof, wherein A represents a direct bond or —O—CH$_2$— (where the oxygen atom is linked to the methylene group at the 4'-position).

(15) Oligonucleotide analogues and pharmacologically acceptable salts thereof, wherein $R_1$ represents a hydrogen atom, an aliphatic acyl group, an aromatic acyl group, a methyl group substituted by 1 to 3 aryl groups, a methyl group substituted by 1 to 3 aryl groups, with the aryl rings being substituted by a lower alkyl, lower alkoxy, halogen or cyano group, or a silyl group.

(16) Oligonucleotide analogues and pharmacologically acceptable salts thereof, wherein $R_1$ represents a hydrogen atom, an acetyl group, a benzoyl group, a benzyl group, a p-methoxybenzyl group, a dimethoxytrityl group, a monomethoxytrityl group, or a tert-butyldiphenylsilyl group.

(17) Oligonucleotide analogues and pharmacologically acceptable salts thereof, wherein B represents a 6-aminopurin-9-yl (i.e. adeninyl) group, a 6-aminopurin-9-yl group having an amino group protected with a protective group for synthesis of nucleic acid, a 2,6-diaminopurin-9-yl group, a 2-amino-6-chloropurin-9-yl group, a 2-amino-6-chloropurin-9-yl group having an amino group protected with a protective group for synthesis of nucleic acid, a 2-amino-6-fluoropurin-9-yl group, a 2-amino-6-fluoropurin-9-yl group having an amino group protected with a protective group for synthesis of nucleic acid, a 2-amino-6-bromopurin-9-yl group, a 2-amino-6-bromopurin-9-yl group having an amino group protected with a protective group for synthesis of nucleic acid, a 2-amino-6-hydroxypurin-9-yl (i.e. guaninyl) group, a 2-amino-6-hydroxypurin-9-yl group having an amino group protected with a protective group for synthesis of nucleic acid, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl (i.e. cytosinyl) group, a 2-oxo-4-amino-1,2-dihydropyrimidin-1-yl group having an amino group protected with a protective group for synthesis of nucleic acid, a 2-oxo-4-amino-5-fluoro-1,2-dihydropyrimidin-1-yl group, a 2-oxo-4-amino-5-fluoro-1,2-dihydropyrimidin-1-yl group having an amino group protected with a protective group for synthesis of nucleic acid, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl (i.e. uracinyl) group, a 2-oxo-4-hydroxy-5-methyl-1,2-dihydropyrimidin-1-yl (i.e. thyminyl) group, a 4-amino-5-methyl-2-oxo-1,2-dihydropyrimidin-1-yl (i.e. 5-methylcytosinyl) group, or a 4-amino-5-methyl-2-oxo-1,2-dihydropyrimidin-1-yl group having an amino group protected with a protective group for synthesis of nucleic acid.

(18) Oligonucleotide analogues and pharmacologically acceptable salts thereof, wherein B represents a benzoylaminopurin-9-yl, adenyl, 2-isobutyrylamino-6-hydroxypurin-9-yl, guaninyl, 2-oxo-4-benzoylamino-1,2-dihydropyrimidin-1-yl, cytosinyl, 2-oxo-5-methyl-4-benzoylamino-1,2-dihydropyrimidin-1-yl, 5-methylcytosinyl, uracinyl or thyminyl group.

The preferred ones, if they contain the structure of the general formula (4), are, for example:

(19) Oligonucleotide analogues and pharmacologically acceptable salts thereof, wherein B represents a 6-aminopurin-9-yl (i.e. adeninyl) group, a 6-aminopurin-9-yl group having an amino group protected with a protective group for synthesis of nucleic acid, a 2,6-diaminopurin-9-yl group, a 2-amino-6-chloropurin-9-yl group, a 2-amino-6-chloropurin-9-yl group having an amino group protected with a protective group for synthesis of nucleic acid, a 2-amino-6-fluoropurin-9-yl group, a 2-amino-6-fluoropurin-9-yl group having an amino group protected with a protective group for synthesis of nucleic acid, a 2-amino-6-bromopurin-9-yl group, a 2-amino-6-bromopurin-9-yl group having an amino group protected with a protective group for synthesis of nucleic acid, a 2-amino-6-hydroxypurin-9-yl (i.e. guaninyl) group, a 2-amino-6-hydroxypurin-9-yl group having an amino group protected with a protective group for synthesis of nucleic acid, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl (i.e. cytosinyl) group, a 2-oxo-4-amino-1,2-dihydropyrimidin-1-yl group having an amino group protected with a protective group for synthesis of nucleic acid, a 2-oxo-4-amino-5-fluoro-1,2-dihydropyrimidin-1-yl group, a 2-oxo-4-amino-5-fluoro-1,2-dihydropyrimidin-1-yl group having an amino group protected with a protective group for synthesis of nucleic acid, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl (i.e. uracinyl) group, a 2-oxo-4-hydroxy-5-methyl-1,2-dihydropyrimidin-1-yl (i.e. thyminyl) group, a 4-amino-5-methyl-2-oxo-1,2-dihydropyrimidin-1-yl (i.e. 5-methylcytosinyl) group, or a 4-amino-5-methyl-2-oxo-1,2-dihydropyrimidin-1-yl group having an amino group protected with a protective group for synthesis of nucleic acid; and

(20) Oligonucleotide analogues and pharmacologically acceptable salts thereof, wherein B represents a benzoylaminopurin-9-yl, adenyl, 2-isobutyrylamino-6-hydroxypurin-9-yl, guaninyl, 2-oxo-4-benzoylamino-1,2-dihydropyrimidin-1-yl, cytosinyl, 2-oxo-5-methyl-4-benzoylamino-1,2-dihydropyrimidin-1-yl, 5-methylcytosinyl, uracinyl or thyminyl group.

The oligonucleotide analogues and salts thereof according to the present invention may contain one or more units having only one of the structures represented by the general formulas (3) and (4), or may contain one or more units having both of the structures represented by the general formulas (3) and (4).

In connection with the above oligonucleotide analogues (15) to (16), (17) to (18) or (19) to (20), the greater their number is, the more preferred these oligonucleotide analogues become. Also preferred are oligonucleotide analogues and pharmacologically acceptable salts thereof obtained by arbitrarily selecting, in the general formula (3), A from (14), $R_1$ from (15) to (16), and B from (17) to (18), or by arbitrarily selecting, in the general formula (4), B from (19) to (20), or by arbitrarily combining the structures of the general formula (3) and/or the general formula (4). Particularly preferred combinations for the general formula (3) are (14)-(15)-(17), (14)-(15)-(18), (14)-(16)-(17), and (14)-(16)-(18).

The nucleoside analogues and oligonucleotide analogues of the present invention can be synthesized in the following manners:

Synthesis of Nucleoside Analogues

The compounds represented by the general formula (1) can be obtained by the following Method A, while the compounds represented by the general formula (2) can be obtained by the following Method B:

(Method A)

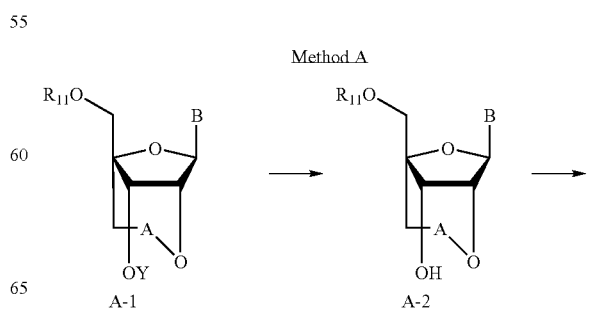

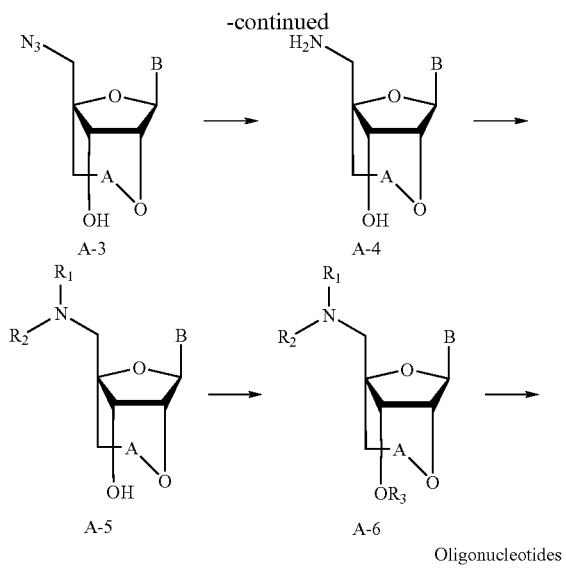

A-3  A-4

A-5  A-6

Oligonucleotides

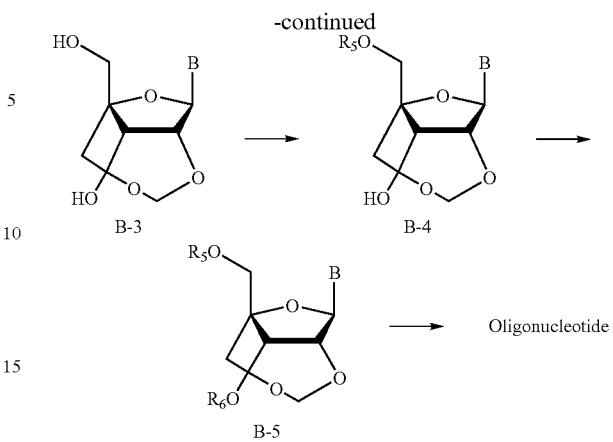

B-3  B-4

B-5

Oligonucleotide

In the Method A, $R_{11}$ represents a group forming a leaving group, Y represents a protective group, and $R_1$, $R_2$, $R_3$, A and B are as defined earlier.

The protected hydroxyl group at the 3'-position of Compound A-1 is subjected to deprotection to obtain Compound A-2, into which an azido group is introduced to obtain Compound A-3. Then, Compound A-3 is converted into an amino compound (Compound A-4). $R_1$ and/or $R_2$ (trityl group optionally substituted by a methoxy group) are or is introduced into Compound A-4 to obtain Compound A-5.

The method of synthesizing Compound A-1, the starting compound, is described, for example, in Japanese Patent Application Laid-Open No. 1998-304889 if A in the general formula (1) is a direct bond, or is described, for example, in Japanese Patent Application Laid-Open No. 2000-297097 if A is an alkylene group having 1 to 4 carbon atoms. If A is —O—$(CH_2)_m$— or —N($R_4$)—$(CH_2)$—, Compound A-1, which is the starting compound, can be obtained in accordance with Method B to be described later.

Examples of the "group forming a leaving group" as $R_{11}$ are a lower alkylsulfonyl group such as methanesulfonyl or ethanesulfonyl, a halogen-substituted lower alkylsulfonyl group such as trifluoromethanesulfonyl, and an arylsulfonyl group such as p-toluenesulfonyl. A preferred example is a methanesulfonyl group or a p-toluenesulfonyl group.

The protective group as Y is the same as the "protective group for a hydroxyl group for synthesis of nucleic acid" as the aforementioned $R_3$. Its preferred example is a benzyl group.

(Method B)

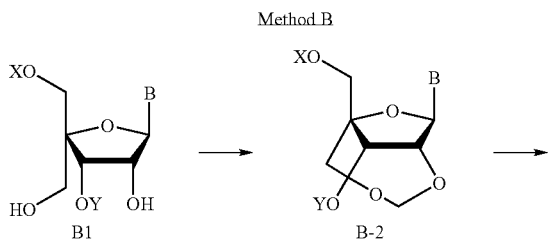

Method B

B1  B-2

In the Method B, X represents a protective group, Y represents a protective group, and $R_5$, $R_6$ and B are as defined earlier. The protective group as X is the same as the "protective group for a hydroxyl group for synthesis of nucleic acid" as the aforementioned $R_5$. Its preferred example is a benzyl group. The protective group as Y is the same as the "protective group for a hydroxyl group for synthesis of nucleic acid" as the aforementioned $R_6$. Its preferred example is a benzyl group.

Compound B-1 is reacted with paraformaldehyde to perform a ring-forming reaction, thereby obtaining Compound B-2. Then, the protective groups for the hydroxyl groups at the 3'-position and the 4'-position are eliminated to obtain Compound B-3. $R_1$ and/or $R_2$ (trityl group optionally substituted by a methoxy group) are or is introduced into Compound B-3 to obtain Compound B-4.

The method of synthesizing Compound B-1, the starting compound, is described, for example, in Tetrahedron 54, 3607-3630 (1998) and Japanese Patent Application Laid-Open No. 2000-297097.

(2) Synthesis of Oligonucleotide Analogues $R_6$ (especially, a phosphonyl group, or a group formed upon reaction with a mono-substituted chloro(alkoxy)phosphine or a di-substituted alkoxyphosphine) is introduced into Compound A-5 or B-4 to obtain Compound A-6 or B-5. Various oligonucleotide analogues are synthesized with the use of a DNA synthesizer. Then, the resulting oligonucleotide analogues are purified by use of a reversed phase column, and the purity of the products is analyzed by reversed phase HPLC, whereby the production of purified oligonucleotide analogues can be confirmed.

The reaction conditions, protective group introducing reagents, and reaction reagents in the aforementioned Method A and Method B can be determined concretely by reference to the methods described in the Examples, but are not limited thereto. The reaction conditions and reagents usable based on common knowledge in the art can be adopted where appropriate. For example, the methods described in Japanese Patent Application Laid-Open No. 2000-297097 and Japanese Patent Application Laid-Open No. 1998-304889 can be referred to. Moreover, if B in the general formula (1) or (2) is any of various natural or non-natural nucleic acid bases and other aromatic heterocyclic rings or aromatic hydrocarbon rings, the starting material for the compounds of the present invention can be synthesized by referring to the method described in Japanese Patent Application Laid-Open No. 1998-304889.

One or more of the compounds belonging to Compound A-6 and/or Compound B-5 can be rendered existent in the oligonucleotide analogues. Alternatively, they may be present at 2 or more positions of the oligonucleotide analogue so as to be separated by one or more natural nucleotides. According to the present invention, it is possible to synthesize oligonucleotide analogues having the nucleotide analogues of the present invention introduced at the necessary positions and in the necessary numbers (over the necessary length). The entire length of the nucleotide analogues is 2 to 50, preferably 8 to 30, nucleotide units.

The nucleotide analogues of the present invention are minimally degraded by nucleases, and can exist for long periods in vivo after administration into living organisms. These nucleotide analogues form double strands with sense RNA, for example, to inhibit transcription into mRNA for formation of a pathogenic in vivo component (protein). The nucleotide analogues are also considered to inhibit the proliferation of infecting virus.

In view of these facts, the nucleotide analogues of the present invention are expected to be useful as pharmaceuticals, including antitumor agents and antiviral agents, which inhibit the action of genes to treat diseases. That is, according to the present invention, there are provided oligonucleotide analogues, which have stable and excellent antisense or antigene activity or excellent activity as drugs for detection of particular genes or as primers for initiation of amplification of particular genes, and nucleoside analogues which are intermediates for production of the oligonucleotide analogues. Concretely, the oligonucleotide analogues of the present invention are useful as materials for various physiologically active or bioactive substances and pharmaceuticals, as functional materials for RNAi and decoy double-stranded oligonucleotides, as functional materials for DNA chips and molecular beacons targeting single-stranded nucleic acids such as cDNA, and as functional materials for uses in various antisense methods (including ribozymes and DNAzymes) or antigene methods. Of these oligonucleotide analogues, the oligonucleotide analogues containing the structure represented by the general formula (3) are easy to synthesize, have high capacity of forming double strands with RNA, and possess excellent resistance to enzymes. Thus, they are particularly suitable for the antisense method. The oligonucleotide analogues containing the structure represented by the general formula (4), on the other hand, have so high a degree of freedom of the ring structure in the 2'-4' configuration that they are suitable for formation of triple strands. Alternatively, such oligonucleotide analogues of the formula (4) are excellent in duplex-forming capacity for RNA and also excellent in enzyme resistance, so that they are particularly suitable for the antigene method or the antisense method.

The nucleotide analogues of the present invention can be formed, for example, into parenteral preparations when mixed with customary adjuvants such as buffers and/or stabilizers. For topical use, they can be mixed with customary pharmaceutical carriers to prepare ointments, creams, liquids and solutions, or plasters.

Synthesis of the oligonucleoside analogues and oligonucleotide analogues of the present invention will be described in greater detail based on the following Examples:

EXAMPLE 1

Synthesis of Nucleoside Analogue

Synthesis of 3'-O-[2-Cyanoethoxy-(diisopropylamino)phosphino]-5'-deoxy-5'-(4-methoxytriphenyl-methylamino)-5-methyl-2'-O,4'-C-methyleneuridine (Compound 7)

EXAMPLE 1

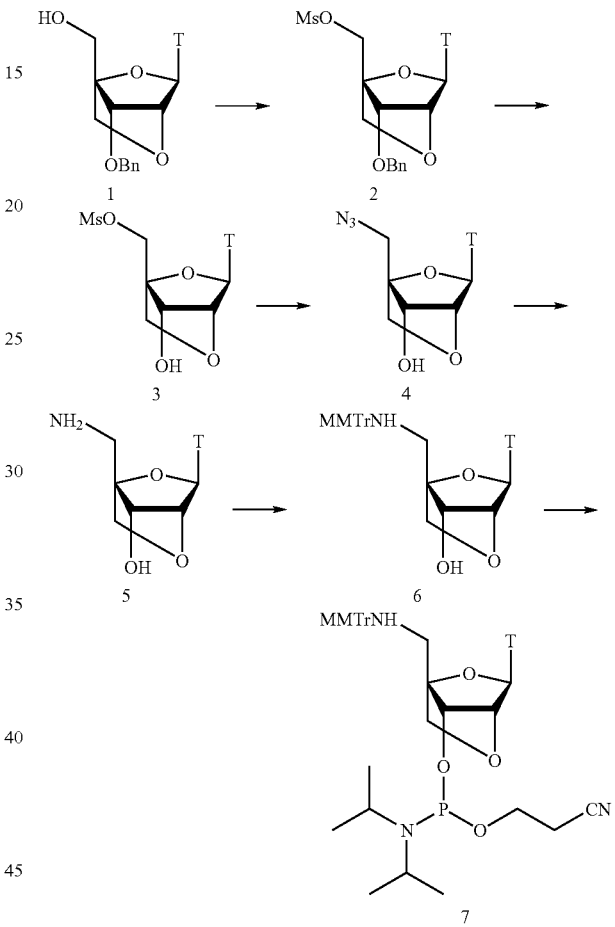

(1) 3'-O-Benzyl-5'-O-mesyl-5-methyl-2'-O,4'-C-methyleneuridine (Compound 2)

In a nitrogen stream, methanesulfonyl chloride (6 µl, 0.083 mmol) was added to a pyridine solution (2.0 ml) of Compound 1 (25 mg, 0.069 mmol), and the mixture was stirred for 1 hour at room temperature. A saturated aqueous solution of sodium bicarbonate was added to the reaction mixture, and then the resulting mixture was extracted with ethyl acetate. The organic layer was washed with water and a saturated aqueous solution of sodium chloride, and then dried over anhydrous sodium sulfate. The solvent was distilled off under reduced pressure, and the resulting crude product was purified by flash silica gel column chromatography (n-hexane: ethyl acetate=1:2) to obtain Compound 2 (30 mg, 99%) as a white powder.

$^1$H-NMR (CDCl$_3$) δ: 1.93 (3H,s), 3.08 (3H,s), 3.89, 4.09 (2H,AB,J=8 Hz), 3.93 (1H,s), 4.53, 4.61 (2H,AB,J=13 Hz), 4.61 (1H,s), 4.56, 4.67 (2H,AB,J=11 Hz), 5.68 (lH,s), 7.26-7.42 (6H,m) and 8.56 (1H,brs). mp. 76-80° C.

(2) 5'-Azido-5'-deoxy-5-methyl-2'-O,4'-C-methyleneuridine (Compound 4)

An ethanol solution of Compound 2 (35 mg, 0.080 mmol) and cyclohexene (0.3 ml, 3.0 mmols) were added to an ethanol suspension of 30 mg of 20% Pd(OH)$_2$/C, and the mixture was heated under reflux for 2 hours. The catalyst was removed by filtration, and the solvent was distilled off under reduced pressure. Then, the resulting 5'-O-mesyl-5-methyl-2'-O,4'-C-methyleneuridine (Compound 3) obtained as a white solid (27 mg) was used for the next reaction without being purified.

A dimethylformamide (3.0 ml) solution of Compound 3 (27 mg, 0.078 mmol) and sodium azide was stirred for 1.5 hours at room temperature and for 2 hours at 100° C. in a stream of nitrogen. The solvent was distilled off under reduced pressure, and then a small amount of water was added to the residue, followed by extracting the mixture with ethyl acetate. The organic layer was washed with a saturated aqueous solution of sodium chloride, and dried over anhydrous sodium sulfate. Then, the solvent was distilled off under reduced pressure to obtain Compound 4 (28 mg, quant. in 2 steps) as a yellow oily substance.

$^1$H-NMR (CDCl$_3$) δ: 1.90 (3H,s), 3.77 (2H,s), 3.84, 4.02 (2H,AB,J=8 Hz), 4.14 (1H,s), 4.58 (1H,s), 5.55 (1H,s), 7.47 (1H,s) and 9.89 (1H,brs). IR (KBr) 2105 cm$^{-1}$ (N$_3$).

(3) 5'-Deoxy-5'-(4-methoxytriphenylmethylamino)-5-methyl-2'-O,4'-C-methyleneuridine (Compound 6)

In a nitrogen stream, triphenylphosphine (49 mg, 0.19 mmol) was added to a pyridine solution (3.0 ml) of Compound 4 (28 mg, 0.095 mmol), and the mixture was stirred for 3 hours at room temperature. A 28% aqueous solution of ammonia (5.0 ml) was added, and the mixture was stirred further for 14 hours. Then, the solvent was distilled off under reduced pressure to obtain 5'-amino-5'-deoxy-5-methyl-2'-O,4'-C-methyleneuridine (Compound 5) as a crude product.

In a nitrogen stream, monomethoxytrityl chloride (32 mg, 0.104 mmol) was added to a pyridine solution (2.0 ml) of Compound 5, and the mixture was stirred for 3 hours at room temperature. A saturated aqueous solution of sodium bicarbonate was added to the reaction mixture, and then the resulting mixture was extracted with ethyl acetate. The organic layer was washed with water and a saturated aqueous solution of sodium chloride, and then dried over anhydrous sodium sulfate. The solvent was distilled off under reduced pressure, and the resulting crude product was purified by flash silica gel column chromatography (chloroform:methanol=9:1) to obtain Compound 6 (45 mg, 87% in 2 steps) as a colorless oily substance.

$^1$H-NMR (CDCl$_3$) δ: 1.91 (3H,s), 2.51, 2.65 (2H,AB,J=14 Hz), 3.74 (3H,s), 3.76, 3.92 (2H,AB,J=8 Hz), 4.25 (1H,s), 4.35 (1H,s), 5.63 (1H,s), 6.76 (2H,d,J=9 Hz), 7.14-7.80 (15H, m) and 8.99 (1H,brs).

(4) 3'-O-[2-Cyanoethoxy(diisopropylamino)phosphino]-5'-deoxy-5'-(4-methoxytriphenylmethylamino)-5-methyl-2'-O,4'-C-methyleneuridine (Compound 7)

In a stream of nitrogen, an acetonitrile-tetrahydrofuran solution (3:1, 4 ml) of Compound 6 (56 mg, 103 μmols) and diisopropylammonium tetrazolide (20 mg, 99 μmols) was added, 2-cyanoethyl N,N,N',N'-tetraisopropylphosphorodiamidite (53 μl, 167 μmols) was added, and the mixture was stirred for 16.5 hours at room temperature. 2-Cyanoethyl N,N,N',N'-tetraisopropylphosphorodiamidite (10 μl, 31 μmols) was further added, and the mixture was stirred for 4 hours. Further, 2-cyanoethyl N,N,N',N'-tetraisopropylphosphorodiamidite (50 μl, 157 μmols) was added, followed by stirring the mixture for 2.5 hours. The solvent was distilled off under reduced pressure, and the resulting crude product was purified by flash silica gel column chromatography (n-hexane:ethyl acetate=1:1) and subsequent reprecipitation (n-hexane-ethyl acetate) to obtain Compound 7 (69 mg, 90%) as a white powder.

$^{31}$P-NMR (acetone-d$_6$) δ: 142.3, 142.5. mp. 74-77° C.

EXAMPLE 2

Synthesis of Nucleoside Analogue

Synthesis of 3'-O-[2-Cyanoethoxy-(diisopropylamino)phosphino]-5'-O-(4,4'-dimethoxytrityl)-2'-O,4'-C-methylenoxymethylene-5-methyluridine (Compound 12)

EXAMPLE 2

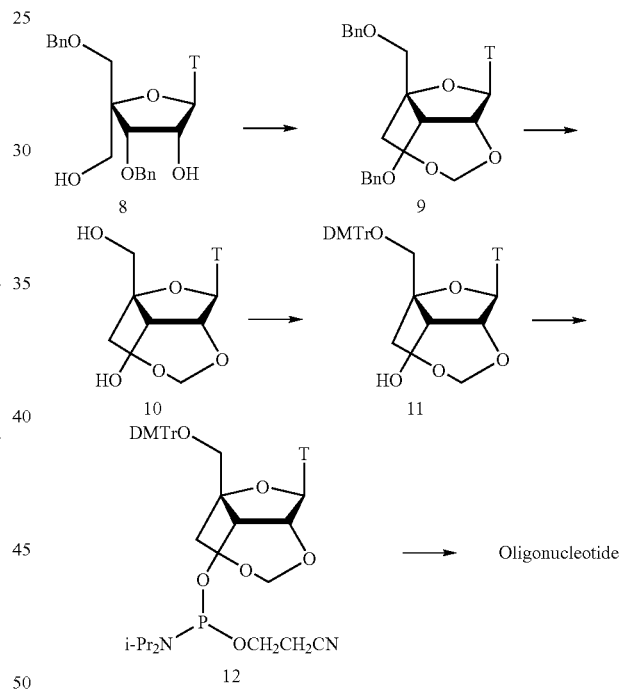

(1) 2'-O,4'-C-Methylenoxymethylene-5-methyluridine (Compound 10)

In a stream of nitrogen, p-toluenesulfonic acid monohydrate (10 mg, 53 μmols) and paraformaldehyde (50 mg) were added to a 1,2-dichloromethane solution of Compound 8 (48 mg, 0.10 mmol: the compound described in J. Wengel et al., Tetrahedron, 54, 3607-3630 (1998)) at room temperature, and the mixture was refluxed for 2 hours. A saturated aqueous solution of sodium bicarbonate was added to the reaction mixture, and then the resulting mixture was extracted with ethyl acetate. The organic layer was washed with water and a saturated aqueous solution of sodium chloride, then dried over anhydrous sodium sulfate, and concentrated under reduced pressure. The resulting residue was purified by flash silica gel column chromatography (n-hexane:ethyl acetate (3:2, v/v)) to obtain Compound 9 (41 mg, 84%) as a white powder.

Mp 65-70° C.

$^1$H-NMR (CDCl$_3$) d: 1.52 (3H, s), 3.54 (1H, d, J=10 Hz), 3.68-3.76 (3H, m), 4.37 (1H, d, J=6 Hz), 4.44 (1H, d, J=6 Hz), 4.50-4.60 (3H, m), 4.79 (1H, d, J=12 Hz), 5.21, 5.31 (2H, AB, J=6 Hz), 6.12 (1H, s), 7.21-7.37 (10H, m), 7.60 (1H, s), 8.07 (1H, brs).

An ethanol solution of Compound 9 (36 mg, ca. 75 mmols) and cyclohexene (0.38 ml, 3.75 mmols) were added to an ethanol suspension of 20% Pd(OH)$_2$/C (25 mg), and the mixture was refluxed for 3 hours. After the mixture was filtered, silica (0.2 g) was added to the filtrate, and the mixture was concentrated under reduced pressure. The residue was purified by flash silica gel column chromatography (chloroform-methanol (12:1, v/v)) to obtain Compound 10 (20 mg, 89%).

mp. 294-295° C. $^1$H-NMR (CD$_3$OD) d: 1.86 (3H, s), 3.65, 3.70 (2H, AB, J=12 Hz), 3.70 (2H, s), 4.18 (1H, d, J=6 Hz), 4.49 (1H, d, J=6 Hz), 5.07, 5.32 (2H, AB, J=6 Hz), 6.05 (1H, s), 7.99 (1H, s).

(2) 5'-O-(4,4'-Dimethoxytrityl)-2'-O,4'-C-methyl-enoxy-methylene-5-methyluridine (Compound 11)

In a stream of nitrogen, dimethoxytrityl chloride (DMTrCl, 266 mg, 0.79 mmol) was added to an anhydrous pyridine (3.0 ml) solution of Compound 10 (157 mg, 0.52 mmol) at room temperature, and the mixture was stirred for 3 hours at room temperature. A saturated aqueous solution of sodium bicarbonate was added to the reaction mixture, and then the resulting mixture was extracted with ethyl acetate. The organic layer was washed with water and a saturated aqueous solution of sodium chloride, then dried over anhydrous sodium sulfate, and then concentrated under reduced pressure. The residue was purified by flash silica gel column chromatography (chloroform-methanol (50:1, v/v)) to obtain Compound 11 (315 mg, 100%) as a white powder.

mp 189-194° C., $^1$H-NMR (acetone-d$_6$) d: 1.42 (3H, s), 3.34. 3.38 (2H, AB, J=11 Hz), 3.70, 3.85 (2H, AB, J=12 Hz), 3.79 (6H, s), 4.34 (1H, d, J=6 Hz), 4.91 (1H, dd, J=6, 6 Hz), 5.07 (1H, d, J=6 Hz), 5.28 (1H, d, J=6 Hz), 5.30 (1H, d, J=6 Hz), 6.16 (1H, s), 6.89 (4H, d, J=8 Hz), 7.24-7.51 (9H, m), 7.60 (1H, s), 9.97 (1H, brs).

(3) 3'-O-[2-Cyanoethoxy(diisopropylamino)phosphino]-5'-O-(4,4'-dimethoxytrityl)-2'-O,4'-C-methyl-enoxymethylene-5-methyluridine (Compound 12)

In a stream of nitrogen, 2-cyanoethyl-N,N,N',N'-tetraisopropylphosphorodiamidite (189 μl, 0.60 mmol) was added to an anhydrous acetonitrile-tetrahydrofuran solution (3:1, 4 ml) of Compound 11 (100 mg, 0.17 mmol) and diisopropylammonium tetrazolide (40 mg, 0.23 mmol) at room temperature, and the mixture was stirred for 4 hours at room temperature, followed by further stirring the mixture at 40° C. for 7 hours. The solvent was distilled off under reduced pressure, and the residue was purified by flash silica gel column chromatography (n-hexane-ethyl acetate (1:1, v/v)) to obtain Compound 12 (107 mg, 80%) as a white powder.

mp 81-87° C. $^{31}$p-NMR (CDCl$_3$) d$_p$: 150.50, 150.83.

EXAMPLE 3

Synthesis of Nucleoside Analogue: N$^4$-benzoyl-2'-O-4'-C-methylenoxymethylenecytidine (Compound 26)

EXAMPLE 3

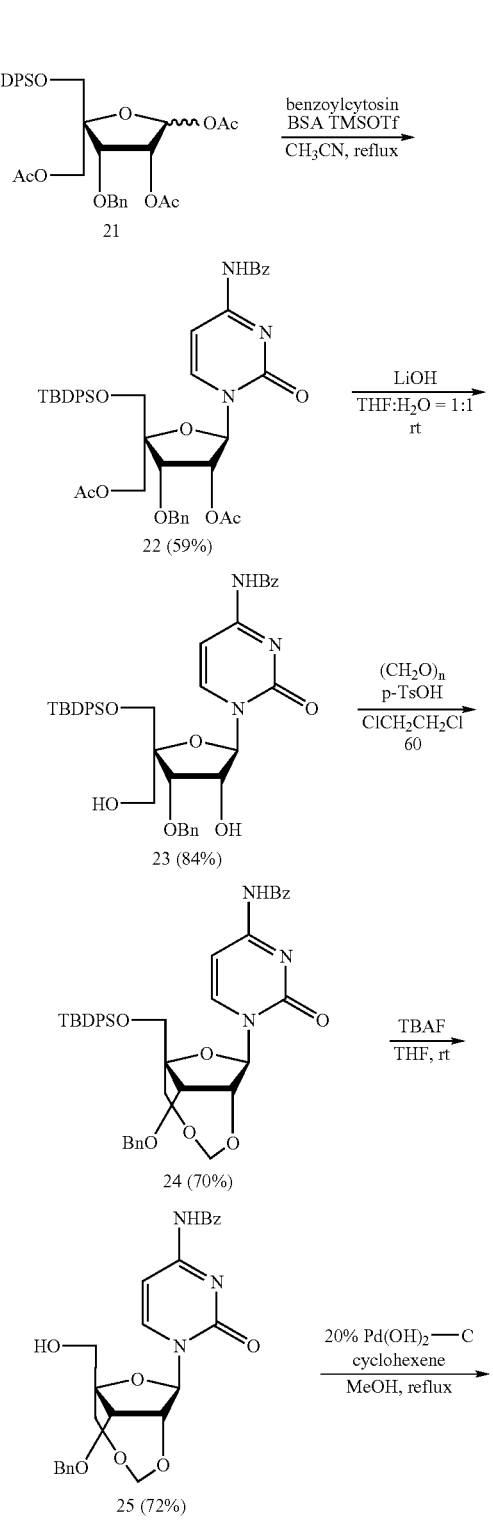

-continued

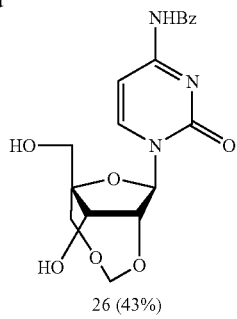

26 (43%)

(1) Synthesis of N⁴-Benzoyl-4'-C-acetoxymethyl-2'-O-acetyl-3'-O-benzyl-5'-O-tert-butyldiphenylsilylcytidine (Compound 22)

In a stream of nitrogen, benzoylcytosine (950 mg, 4.40 mmols) and N,O-bis(trimethylsilyl)acetamide (1.67 ml, 11.7 mmols) were added to an anhydrous acetonitrile solution (30 ml) of Compound 21 (1.86 g, 2.93 mmols), and the mixture was heated under reflux for 2 hours. The mixture was cooled to 0° C., and trimethylsilyltrifluoromethanesulfonic acid (0.26 ml, 1.47 mmols) was added dropwise. The mixture was heated under reflux for 6 hours, and then the reaction mixture was added dropwise to a saturated aqueous solution of sodium bicarbonate. The resulting solution was extracted with ethyl acetate, whereafter the organic layer was washed with water and a saturated aqueous solution of sodium chloride in this order, and then dried over sodium sulfate. The solvent was distilled off, and then the residue was purified by silica gel column chromatography (n-hexane:ethyl acetate=3:2) to obtain Compound 22 (1.37 g, 59%) as a white powder.

$^1$H-NMR (CDCl$_3$) d:1.12 (9H, s), 1.94 (3H, s), 2.12 (3H, s), 3.77, 4.03 (2H, AB, J=11 Hz), 4.51 (1H, d, J=4 Hz), 4.54, 4.13 (2H, AB, J=12 Hz), 4.60, 4.20 (2H, AB, J=11 Hz), 5.51 (1H, dd, J=4 Hz, 4 Hz), 6.24 (1H, d, J=4 Hz), 7.65-7.2 (19H, m), 7.90 (2H, d, J=7 Hz), 8.12 (1H, d, J=7 Hz), 8.81 (1H, brs). mp 135-140° C.

(2) Synthesis of N⁴-Benzoyl-3'-O-benzyl-5'-0-tert-butyldiphenylsilyl-4'-C-hydroxymethylcytidine (Compound 23)

In a stream of nitrogen, lithium hydroxide monohydrate (1.60 g, 38.2 mmols) was added to a solution of Compound 22 (6.50 g, 8.23 mmols) in tetrahydrofuran:water=1:1 (90 ml), followed by stirring the mixture for 2 hours. After addition of lithium hydroxide monohydrate (500 mg, 11.9 mmols), the mixture was further stirred for 2 hours. Then, the reaction mixture was extracted with ethyl acetate, whereafter the organic layer was washed with water and a saturated aqueous solution of sodium chloride in this order, and then dried over sodium sulfate. The solvent was distilled off, and then the residue was recrystallized from ethyl acetate to obtain Compound 23 (5.24 g, 84%) as a white solid.

$^1$H-NMR(CDCl$_3$) d: 1.07 (9H, s), 3.11 (1H, brs), 3.68, 3.85 (2H, AB, J=11 Hz), 3.68, 3.85 (2H, AB, J=11 Hz), 4.32 (1H, d, J=6 Hz), 4.36 (1H, brs), 4.47, 4.84 (2H, AB, J=11 Hz), 4.82 (1H, brs), 6.11 (1H, s), 7.21-7.61 (19H, m), 7.91 (2H, d, J=7 Hz), 8.14 (1H, d, J=7 Hz), 8.93 (1H, brs). mp 144-145° C.

(3) Synthesis of N⁴-Benzoyl-3'-O-benzyl-5'-O-tert-butyldiphenylsilyl-2'-O-4'-C-methylenoxymethyl-enecytidine (Compound 24)

In a stream of nitrogen, p-toluenesulfonic acid monohydrate (130 mg, 0.68 mmol) was added to an anhydrous dichloroethane solution (20 ml) of Compound 23 (324 mg, 0.46 mmol), and the mixture was heated to 60° C. Paraformaldehyde (41 mg) was added to the resulting solution, and the mixture was stirred for 90 minutes at 60° C. After addition of paraformaldehyde (50 mg), the mixture was further stirred for 2 hours. Then, the reaction mixture was cooled with ice, and then a saturated aqueous solution of sodium bicarbonate was added. The resulting solution was extracted with ethyl acetate, whereafter the organic layer was washed with water and a saturated aqueous solution of sodium chloride in this order, and dried over sodium sulfate. The solvent was distilled off, and then the residue was purified by silica gel column chromatography (n-hexane:ethyl acetate=2:3) to obtain Compound 24 (230 mg, 70%) as a white solid.

$^1$H-NMR (CDCl$_3$) d: 2.25 (1H, brs), 3.68-3.85 (4H, m), 4.53, 4.57 (2H, AB, J=6 Hz), 4.57 (1H, d, J=11 Hz), 4.80 (1H, d, J=11 Hz), 5.25, 5.37 (2H, AB, J=6 Hz), 6.13 (1H, s), 7.25-7.39 (15H, m), 7.48-7.64 (4H, m), 7.87 (2H, d, J=8 Hz), 8.24 (1H, d, J=8 Hz), 8.73 (1H, brs). mp 102-105° C.

(4) Synthesis of N⁴-Benzoyl-3'-O-benzyl-2'-O-4'-C-methylenoxymethylenecytidine (Compound 25)

In a stream of nitrogen, a THF solution (1.9 ml) of 1M TBAF was added to an anhydrous THF solution (30 ml) of Compound 24 (1.05 g, 1.46 mmols), and the mixture was stirred for 18 hours. The solvent was distilled off, and the residue was purified by silica gel column chromatography (n-hexane:ethyl acetate=1:3) to obtain Compound 25 (504 mg, 72%) as a white solid.

$^1$H —NMR (CDCl$_3$) d: 2.38 (1H, brs), 3.70, 3.86 (2H, ABq, J=12 Hz), 3.73, 3.78 (2H, AB, J=12 Hz), 4.52, 4.57 (2H, AB, J=6 Hz), 4.57 (1H, d, J=12 Hz), 4.80 (1H, d, J=12 Hz), 5.25, 5.37 (2H, AB, J=6 Hz), 6.15 (1H, s), 7.29-7.39 (5H, m), 7.47-7.63 (4H, m), 7.86 (2H, d, J=7 Hz), 8.28 (1H, d, J=7 Hz), 8.74 (1H, brs). mp 242-243° C.

(5) Synthesis of N⁴-Benzoyl-2'-O-4'-C-methylenoxymethylenecytidine (Compound 26)

In a stream of nitrogen, palladium hydroxide-activated carbon (68 ml) and cyclohexene (0.17 ml, 1.7 mmols) were added to an anhydrous methanol solution (15 ml) of Compound 25 (86 mg, 0.17 mmol), and the mixture was heated under reflux for 3 hours. After filtration of the reaction mixture, silica gel (0.2 g) was added to the filtrate, and the solvent was distilled off. The residue was purified by silica gel column chromatography (chloroform:methanol=12:1) to obtain Compound 26 (30 mg, 43%) as a white solid.

$^1$H-NMR (CD$_3$OD) d: 3.52-3.66 (4H, m), 4.50 (1H, d, J=11 Hz), 4.62 (1H, d, J=11 Hz), 5.01, 5.20 (2H, AB, J=6 Hz), 5.77 (1H, d, J=8 Hz), 5.99 (1H, s), 7.15-7.26 (5H, m), 8.03 (1H, d, J=8 Hz).

EXAMPLE 4

Synthesis of Oligonucleotide Analogue Containing Nucleoside Analogue

An oligonucleotide analogue containing Compound 12 was synthesized on a 0.2 μmol scale by means of Expedite™ 8909 (a product of ABI) in accordance with a standard phosphoroamidite protocol. The coupling time for coupling of amidite units (Compound 12) to the hydroxyl group at the 5'-terminal was prolonged from 2 minutes (standard conditions) to 45 minutes. An oligonucleotide analogue protected by the DMTr group at the 5'-terminal and supported in a solid phase was treated with concentrated ammonium hydroxide for 18 hours at 60° C., and the solvent was distilled off. The resulting crude product was roughly purified using NEN- SORB™ PREP, and then purified by reversed phase HPLC (WakoPak® WS-DNA column, 10 mm×250 mm).

The purity of the synthesized oligonucleotide analogue was confirmed by reversed phase HPLC (WakoPak® WS-DNA column, 4.6 mm×250 mm) (conditions: a gradient of 8-16% acetonitrile for 30 minutes at a rate of 1 ml/min in a 0.1M trimethylammonium acetate buffer (pH 7.0)). The molecular weight was determined by MALDI-TOF-MASS measurement.

An oligonucleotide analogue containing Compound 7 was also synthesized by the same method as described above.

The oligonucleotide analogues synthesized are as follows:

TABLE 1

Oligonucleotide analogues containing Compound 7 (indicated by X in the table)

| No. | Oligonucleotide analogue |
|---|---|
| 7-1 | 5'-TTTTTXTTTT-3' |
| 7-2 | 5'-TXXXXXXXXT-3' |
| 7-3 | 5'-TTTTXTXTXT-3' |
| 7-4 | 5'-TTTTTTTTXT-3' |
| 7-5 | 5'-TXTTTTTTTT-3' |

TABLE 2

Oligonucleotide analogues containing Compound 12 (indicated by X in the table) (Part 1)
5'-TCTTCNNNNNCTCTCT-3' (C denotes 2'-deoxy-5-methylcytidine)

| No. | NNNNN | Reversed phase HPLC retention time (min) | Yield (%) |
|---|---|---|---|
| 12-1 | 5'-TTXTT-3' | 17.8 | 33 |
| 12-2 | 5'-TXXXT-3' | 18.5 | 33 |
| 12-3 | 5'-XTXTX-3' | 19.3 | 22 |
| 12-4 | 5'-XXXXX-3' | 19.2 | 15 |

TABLE 3

Oligonucleotide analogue containing Compound 12 (indicated by X in the table) (Part 2)

| No. | | Reversed phase HPLC retention time (min) | Yield (%) |
|---|---|---|---|
| 12-5 | 5'-TTTTTCTXTCTCTCT-3' | 18.8 | 33 |

In the table, C denotes 2'-deoxy-5-methylcytidine.

TABLE 4

Oligonucleotide analogues containing Compound 12 (indicated by X in the table) (Part 3)
5'-GCGNNNNNNGCT-3'

| No. | NNNNNN |
|---|---|
| 12-6 | TTTTTT |
| 12-7 | TTXTTT |
| 12-8 | TTXTXT |
| 12-9 | XTXTXT |
| 12-10 | TTXXXT |
| 12-11 | XXXXXX |

EXPERIMENTAL EXAMPLE 1

Measurement (1) of Melting Temperature (Tm)

The Tm values of annealing products formed from the oligonucleotide strands 7-1 to 7-5 (antisense strands) synthesized in the Example and sense strands were measured to examine the hybridizing capacity of the antisenses.

A sample solution (500 μl) with end concentrations of NaCl 150 mM, sodium phosphate buffer (pH 7.2) 10 mM, antisense strand 2 μM, and sense strand 2 μM was bathed in boiling water, and cooled to room temperature over 10 hours. While a nitrogen stream was passed into a cell chamber of a spectrophotometer (Shimadzu, UV-2100PC) for prevention of dew formation, the sample solution was gradually cooled to 5° C., and further held at 10° C. for 20 minutes, whereafter measurement was started. The temperature of the sample was raised to 90° C. at a rate of 0.2° C./minute, and ultraviolet absorption at 260 nm was measured at intervals of 0.1° C. To prevent changes in the concentration with increases in the temperature, a capped cell was used, and a drop of mineral oil was added to the surface of the sample solution, followed by making the measurement.

The results are shown in Table 5.

TABLE 5

| | | Tm (ΔTm/unit modification) (° C.) | |
|---|---|---|---|
| | | Sense strand | |
| | Antisense strand | Poly A | Poly dA |
| Natural type | 5'-TTTTTTTTTT-3' | 24 | 28 |
| 7-1 | 5'-TTTTTXTTTT-3' | 30(+6.0) | 27(-1.0) |
| 7-2 | 5'-TXXXXXXXXT-3' | 47(+2.9) | 39(+1.4) |
| 7-3 | 5'-TTTTXTXTXT-3' | 58(+11.3) | 19(-3.0) |
| 7-4 | 5'-TTTTTTTTXT-3' | 29(+5.0) | 28(0) |
| 7-5 | 5'-TXTTTTTTTT-3' | 31(+7.0) | 27(-1.0) |

The above results show that the nucleotide analogues of the present invention have high affinity for single-stranded RNA, as compared with affinity for single-stranded DNA, and they are believed to be suitable for the antisense method.

EXPERIMENTAL EXAMPLE 2

Measurement (2) of Melting Temperature (Tm)

The oligonucleotide strand 7-3 synthesized in the Example was examined for triple strand forming capacity for double-stranded DNA (hairpin DNA) by the same method as in Experimental Example 1.

The results and experimental conditions are shown in Table 6.

TABLE 6

|  | Antisense strand | Tm (° C.) |
|---|---|---|
| Natural type | 5'-TTTTTTTTTT-3' | ND |
| 7-3 | 5'-TTTTXTXTXT-3' | 29 |

Experimental conditions: 150 mM NaCl, 10 mM Na$_2$HPO$_4$ buffer (pH 7.0), 10 mM MgCl$_2$, each strand 2 μM, from 5° C. to 90° C. (0.5° C./min).
ND: Not detected.
Target double strand (hairpin DNA): 5'-AAAAAAAAAAC$_4$
3'-TTTTTTTTTT Table 6 shows that the natural type oligonucleotide showed no triple strand forming capacity for the double-stranded DNA, while the oligonucleotide analogue of the present invention showed triple strand forming capacity for the double-stranded DNA and was thus considered to be useful for the antigene method as well.

EXPERIMENTAL EXAMPLE 3

Measurement (3) of Melting Temperature (Tm)

The oligonucleotide strand 12-5 synthesized in the Example was examined for triple strand forming capacity for double-stranded DNA by the same method as in Experimental Example 1.

The results and experimental conditions are shown in Table 7.

TABLE 7

Compound 12-5: 5'-d(TTTTTCTXTCTCT)-3'
Target double strand:
5'-d(GCTAAAAAGAYAGAGAGATCG)-3'
3'-d(CGATTTTTCTZTCTCTCTAGC)-5'

| | Tm (° C.) Y · Z | | | |
|---|---|---|---|---|
| X | C · G | G · C | T · A | A · T |
| T | 25 | 20 | 17 | 44 |
| 12 | 28 | 21 | 15 | 46 |

Experimental conditions:
150 mM KCl, 7 mM Na$_2$HPO$_4$ buffer (pH 7.0), 10 mM MgCl$_2$, each strand 1.5 μM, from 5° C. to 85° C. (0.5° C./min).

In Table 7, 12 denotes Compound 12 of the present invention, and C signifies 2'-deoxy-5-methylcytidine. Table 7 shows that the oligonucleotide analogue containing Compound 12 of the present invention formed triple strands with the target double strands with high sequence selectivity.

EXPERIMENTAL EXAMPLE 4

Measurement (4) of Melting Temperature (Tm)

The oligonucleotide strands 12-1 to 12-4 synthesized in the Example were examined for double strand forming capacity for single-stranded RNA and single-stranded DNA and triple strand forming capacity for double-stranded DNA by the same method as in Experimental Example 1.

The results and experimental conditions are shown in Table 8.

Sense strand:
5'-TCTTCNNNNNCTCT-3'
Target double-strandedDNA:
5'-GCTAGAAGAAAAGAGATC-3'
3'-CGATCTTCTTTTTCTCTAG-3'
Target single-stranded DNA or RNA:
5'-AGAAGAAAAAGAGA-3'

| | | Tm (° C.) | | |
|---|---|---|---|---|
| | | Triple strand forming capacity | Double strand forming capacity | |
| No. | NNNNN | Double-stranded DNA | Single-stranded DNA | Single-stranded RNA |
| Natural type | 5'-TTTTT-3' | 38 | 47 | 50 |
| 12-1 | 5'-TTXTT-3' | 39 | 45 | 51 |
| 12-2 | 5'-TXXXT-3' | 41 | 41 | 55 |
| 12-3 | 5'-XTXTX-3' | 42 | 40 | 56 |
| 12-4 | 5'-XXXXX-3' | 36 | 39 | 60 |

In Table 8C signifies 2'-deoxy-5-methylcytidine. Table 8 shows that the oligonucleotide analogues containing Compound 12 of the present invention have high double strand forming capacity for single-stranded RNA as compared with the natural type, and also have superior triple strand forming capacity.

Similarly, the oligonucleotide strands 12-6 to 12-11 synthesized in the above Example were examined for double strand forming capacity for single-stranded RNA and single-stranded DNA by the same method as in Experimental Example 1.

The results and experimental conditions are shown in Table 9.

TABLE 9

Results of Tm measurements
Sense strand:
5'-GCGXXXXXXGCT-3'
Target single strand:
3'-CGCAAAAAACGA-5'

| | ssDNA Tm (ΔTm) | | | | ssRNA Tm (ΔTm) | | | |
|---|---|---|---|---|---|---|---|---|
| No. | 1st | 2nd | 3rd | average | 1st | 2nd | 3rd | average |
| 12-6 | 51.2 | 50.5 | 50.6 | 50.8 | 46.5 | 46.6 | 46.6 | 46.6 |
| 12-7 | 46.7 | 47.1 | 47.6 | 47.1 (−3.7) | 47.0 | 47.1 | 47.6 | 47.2 (0.6) |
| 12-8 | 45.2 | 44.5 | 45.6 | 45.1 (−2.9) | 48.5 | 48.6 | 48.6 | 48.6 (1.0) |

TABLE 9-continued

Results of Tm measurements
Sense strand:
5'-GCGXXXXXXGCT-3'
Target single strand:
3'-CGCAAAAAACGA-5'

| No. | ssDNA Tm (ΔTm) | | | | ssRNA Tm (ΔTm) | | | |
|---|---|---|---|---|---|---|---|---|
|  | 1st | 2nd | 3rd | average | 1st | 2nd | 3rd | average |
| 12-9 | 43.7 | 43.1 | 43.1 | 43.3 (−2.5) | 53.5 | 53.6 | 52.6 | 53.2 (2.2) |
| 12-10 | 43.7 | 44.0 | 44.2 | 44.0 (−2.3) | 50.6 | 50.6 | 51.6 | 50.9 (1.4) |
| 12-11 | 44.1 | 44.5 | 45.1 | 44.6 (−1.0) | 60.1 | 60.6 | 59.9 | 60.2 (2.3) |

The results of Table 9 show that the oligonucleotide analogues containing Compound 12 of the present invention have high double strand forming capacity for single-stranded DNA and single-stranded RNA.

EXPERIMENTAL EXAMPLE 5

Measurement of Enzyme Resistance

The natural type and non-natural type oligonucleotides described below were examined for resistance to exonuclease which degrades an oligonucleotide, starting on its 3' side.

A buffer solution of snake venom phosphodiesterase (0.2 µg) was mixed with a buffer solution (320 µl) of the oligonucleotide (10 µg) held at 37° C. for 15 minutes. Increases in the ultraviolet absorption (260 nm) according to the degradation of the oligomer were measured over time at 37° C. using SHIMADZU UV-2100PC. The buffer used consisted of 50 mM Tris HCl (pH 8.0) and 10 mM $MgCl_2$, and was sufficiently deaerated before measurement.

The sequences of the oligonucleotides used for measurement are shown below.

Natural type:    5'-TTTTTTTTTT-3'
7-4:             5'-TTTTTTTTXT-3'

The changes with time in the ultraviolet absorption are shown in Table 10 and FIG. 1. In Table 10 and FIG. 1, "% of (10mer+9mer) ODN" refers to the remaining rate (%, proportion as absorbance) of the undegraded oligonucleotide (10mer) and an oligonucleotide having one nucleotide on the 3' side removed (9mer, i.e., 5'-TTTTTTTTT-3' for the natural type, and 5'-TTTTTTTTX-3' for Compound 7-4) relative to the undegraded oligonucleotide (10mer) at point 0 in time.

TABLE 10

| Oligonucleotide | % of (10mer + 9mer) ODN | | | | | | | |
|---|---|---|---|---|---|---|---|---|
|  | 0 | 5 | 10 | 20 | 40 | 90 | 180 | (min) |
| 7-4 | 100 | 57 | 44 | 18 | 0 | 0 | 0 |  |
| Natural type | 100 | 0 | 0 | 0 | 0 | 0 | 0 |  |

The result of Table 10 and FIG. 1 show that the oligonucleotide analogues of the present invention have excellent enzyme resistance in comparison with the natural type oligonucleotide.

The invention claimed is:

1. A compound of the following general formula (1) or a salt thereof:

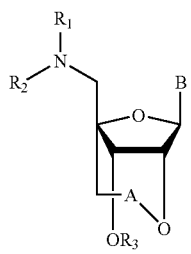

wherein

A represents a direct bond or —O—(CH2)— (wherein an oxygen atom is linked to a methylene group at the 4'-position)

B represents a purin-9-yl group, a 2-oxo-pyrimidin-1-yl group, or a purin-9-yl group or a 2-oxo-pyrimidin-1-yl group which has a substituent selected from the following α group:

α group: a hydroxyl group, a hydroxyl group protected with a protective group for synthesis of nucleic acid, an alkoxy group having 1 to 5 carbon atoms, a mercapto group, mercapto group protected with a protective group for synthesis of nucleic acid, an alkylthio group having 1 to 5 carbon atoms, an amino group, an amino group protected with a protective group for synthesis of nucleic acid, an amino group substituted by an alkyl group having 1 to 5 carbon atoms, an alkyl group having 1 to 5 carbon atoms, and a halogen atom, $R_1$ and $R_2$ are identical or different, and each represents a hydrogen atom, a protective group for an amino group for synthesis of nucleic acid, an alkyl group, an alkenyl group, a cycloalkyl group, an aryl group, an aralkyl group, an acyl group, a silyl group —P(O) ($R_7$)$R_8$ or —P($R_7$)$R_8$ where $R_7$ and $R_8$ are identical or different, and each represents a hydroxyl group, a hydroxyl group protected with a protective group for synthesis of nucleic acid, a mercapto group, a mercapto group protected with a protective group for synthesis of nucleic acid, an amino group, an alkoxy group having 1 to 5 carbon atoms, an alkylthio group having 1 to 5 carbon atoms, a cyanoalkoxy group having 1 to 6 carbon atoms, or an amino group substituted by an alkyl group having 1 to 5 carbon atoms, and $R_3$ represents a hydrogen atom, aliphatic acyl group, an aromatic acyl group, a methyl group substituted by 1 to 3 aryl groups, a methyl group substituted by 1 to 3 aryl groups, with aryl rings being substituted by a lower alkyl, lower alkoxy, halogen or cyano group, a silyl group, a phosphoroamidite group, or —P(O) ($R_7$)$R_8$.

2. The compound or salt thereof according to claim 1, wherein $R_1$ and $R_2$ are identical or different and each represents a hydrogen atom, an aliphatic acyl group, an aromatic acyl group, a methyl group substituted by 1 to 3 aryl groups, a methyl group substituted by 1 to 3 aryl groups, with aryl rings being substituted by a lower alkyl, lower alkoxy, halogen or cyano, or a silyl group.

3. The compound or salt thereof according to claim 1, wherein $R_1$ and $R_2$ are identical or different and each represent a hydrogen atom, an acetyl group, a benzoyl group, a benzyl group, a p-methoxybenzyl group, a dimethoxytrityl group, a monomethoxytrityl group, or a tert-butyldiphenylsilyl group.

4. The compound or salt thereof according to claim 1, wherein $R_3$ represents a hydrogen atom, an acetyl group, a benzoyl group, a benzyl group, a p-methoxybenzyl group, a tert-butyldiphenylsilyl group, —P(OC$_2$H$_4$CN) (N(i-Pr)$_2$), —P(OCH$_3$) (N(i-Pr)$_2$), or a 2-chlorophenyl- or 4-chlorophenylphosphate group.

5. The compound or salt thereof according to claim 1, wherein B represents a 6-aminopurin9-yl group also known as an adeninyl group, a 6aminopurin-9-yl group having an amino group protected with a protective group for synthesis of nucleic acid, a 2,6-diaminopurin-9-yl group, a 2-amino-6-chloropurin-9-yl group, a 2-amino-6-chloropurin-9-yl group having an amino group protected with a protective group for synthesis of nucleic acid, a 2-amino-6-fluoropurin-9-yl group, a 2amino-6-fluoropurin-9-yl group having an amino group protected with a protective group for synthesis of nucleic acid, a 2-amino-6-bromopurin-9-yl group, a 2-amino-6-bromopurin-9-yl group having an amino group protected with a protective group for synthesis of nucleic acid, a 2-amino-6-hydroxypurin-9-yl group also known as a guaninyl group, a 2-amino-6-hydroxypurin-9-yl group having an amino group protected with a protective group for synthesis of nucleic acid, a 6amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group also known as a cytosinyl group, a 2-oxo-4-amino-1,2-dihydropyrimidin-1-yl group having an amino group protected with a protective group for synthesis of nucleic acid, a 2-oxo-4-amino-5-fluoro-1,2-dihydropyrimidin-1-yl group, a 2-oxo-4-amino-5-fluoro-1,2-dihydropyrimidin-1-yl group having an amino group protected with a protective group for synthesis of nucleic acid, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2oxo-4-hydroxy-1,2-dihydropyrimidin-1-yl group also known as a uracinyl group, a 2-oxo-4-hydroxy-5-methyl-1,2-dihydropyrimidin-1-yl group also known as a thyminyl group, a 4-amino-5-methyl-2-oxo-1,2-dihydropyrimidin-1-yl group also known as a 5-methylcytosinyl group, or a 4-amino-5-methyl-2-oxo-1,2-dihydropyrimidin-1-yl group having an amino group protected with a protective group for synthesis of nucleic acid.

6. The compound or a salt thereof according to claim 1, wherein

B represents a 2-oxo-pyrimidin-1-yl group, or a 2-oxo-pyrimidin-1-yl group which has a substituent selected from:

a hydroxyl group, a hydroxyl group protected with a protective group for synthesis of nucleic acid, an alkoxy group having 1 to 5 carbon atoms, a mercapto group, a mercapto group protected with a protective group for synthesis of nucleic acid, an alkylthio group having 1 to 5 carbon atoms, an amino group, an amino group protected with a protective group for synthesis of nucleic acid, an amino group substituted by an alkyl group having 1 to 5 carbon atoms, an alkyl group having 1 to 5 carbon atoms, or a halogen atom.

7. The compound or salt thereof according to claim 1, wherein

B represents a 2-oxo-4-amino-1,2-dihydropyrimidin-1-yl group also known as cytosinyl group, a 2-oxo-4-amino-1,2-dihydropyrimidin-1-yl group having an amino group protected with a protective group for synthesis of nucleic acid, a 2-oxo-4-amino-5-fluoro-1,2-dihydropyrimidin-1-yl group, a 2-oxo-4-amino-5-fluoro-1,2-dihydropyrimidin-1-yl group having an amino group protected with a protective group for synthesis of nucleic acid, a 4-amino-2-oxo-5-chloro-1,2-dihydropyrimidin-1-yl group, a 2-oxo-4-methoxy-1,2-dihydropyrimidin-1-yl group, a 2oxo-4-mercapto-1,2-dihydropyrimidin-1-yl group, a 2-oxo-4-hydroxy-1,2-dihydropyrimidin-1-yl group also known as uracinyl group, a 2-oxo-4-hydroxy-5-methyl-1,2-dihydropyrimidin-1-yl group also known as thyminyl group, a 4-amino-5-methyl-2-oxo-1,2-dihydropyrimidin-1-yl group also known as 5-methylcytosinyl group, or a 4-amino-5-methyl-2-oxo-1,2-dihydropyrimidin-1-yl group having an amino group protected with a protective group for synthesis of nucleic acid, $R_1$ and $R_2$ are identical or different, and each represent a hydrogen atom, a protective group for an amino group for synthesis of nucleic acid, an alkyl group, an alkenyl group, a cycloalkyl group, an aryl group, an aralkyl group, an acyl group, a silyl group, —P(O) $(R_7)R_8$, or $P(R_7)R_8$ wherein $R_7$ and $R_8$ are identical or different, and each represent a hydroxyl group, a hydroxyl group protected with a protective group for synthesis of nucleic acid, a mercapto group, a mercapto group protected with a protective group for synthesis of nucleic acid, an amino group, an alkoxy group having 1 to 5 carbon atoms, an alkylthio group having 1 to 5 carbon atoms, a cyanoalkoxy group having 1 to 6 carbon atoms, or an amino group substituted by an alkyl group having 1 to 5 carbon atoms, and $R_3$ represents a hydrogen atom, an aliphatic acyl group, an aromatic acyl group, a methyl group substituted by 1 to 3 aryl groups, a methyl group substituted by 1 to 3 aryl groups, with aryl rings being substituted by a lower alkyl, lower alkoxy, halogen or cyano, a silyl group, a phosphoroamidite group, or —P(O) $(R_7)R_8$ wherein $R_7$ and $R_8$ are defined above.

8. The compound or a salt thereof according to claim 1, wherein

B represents a 2-oxo-pyrimidin-1-yl group which has (a) substituent(s) selected from:

a hydroxyl group, a hydroxyl group protected with a protective group for synthesis of nucleic acid, and a methyl group.

9. The compound or salt thereof according to claim 1, wherein

B represents a 2-oxo-4-hydroxy-5-methyl-1,2-dihydropyrimidin-1yl group also known as thyminyl group, $R_1$ and $R_2$ are identical or different, and each represent a hydrogen atom, or a protective group for an amino group for synthesis of nucleic acid, and $R_3$ represents a hydrogen atom, or —P(o) $(R_7)R_8$ wherein $R_7$ and $R_8$ are identical or different, and each represent a cyanoalkoxy group having 1 to 6 carbon atoms, or an amino group substituted by an alkyl group having 1 to 5 carbon atoms.

10. A compound of the following general formula (2) or a salt thereof:

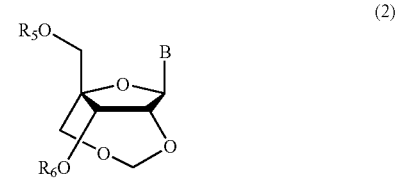

wherein

B represents a purin9-yl group, a 2-oxo-pyrimidin-1-yl group, or a purin-9-yl group or a 2-oxo-pyrimidin-1-yl group which has a substituent selected from the following U group:

α group: a hydroxyl group, a hydroxyl group protected with protective group for synthesis of nucleic acid, an alkoxy group having 1 to 5 carbon atoms, a mercapto group, a mercapto group protected with a protective group for synthesis of nucleic acid, an alkylthio group having 1 to 5 carbon atoms, an amino group, an amino group protected with a protective group for synthesis of nucleic acid, an amino group substituted by an alkyl group having 1 to 5 carbon atoms, an alkyl group having 1 to 5 carbon atoms, and a halogen atom, and $R_5$ and $R_6$ are identical or different, and each represents a hydrogen atom, a protective group for a hydroxyl group for synthesis of nucleic acid, an alkyl group, an alkenyl group, a cycloalkyl group, an aryl group, an aralkyl group, an acyl group, a silyl group, a phosphate group, —P(O) $(R_9)R_{10}$ or —P(R9)R10 wherein $R_9$ and $R_{10}$ are identical or different, and each represents a hydroxyl group, a hydroxyl group protected with a protective group for synthesis of nucleic acid, a mercapto group, a mercapto group protected with a protective group for synthesis of nucleic acid, an amino group, an alkoxy group having 1 to 5 carbon atoms, an alkylthio group having 1 to 5 carbon atoms, a cyanoalkoxy group having 1 to 6 carbon atoms, or an amino group substituted by an alkyl group having 1 to 5 carbon atoms.

11. The compound or salt thereof according to claim 10, wherein $R_5$ represents a hydrogen atom, an aliphatic acyl group, an aromatic acyl group, a methyl group substituted by 1 to 3 aryl groups, a methyl group substituted by 1 to 3 aryl groups, with aryl rings being substituted by a lower alkyl, lower alkoxy, halogen or cyano, or a silyl group.

12. The compound or salt thereof according to claim 10, wherein $R_5$ represents a hydrogen atom, an acetyl group, a benzoyl group, a benzyl group, a p-methoxybenzyl group, a dimethoxytrityl group, a monomethoxytrityl group, or a tert-butyldiphenylsilyl group.

13. The compound or salt thereof according to claim 10, wherein $R_6$ represents a hydrogen atom, an aliphatic acyl group, an aromatic acyl group, a methyl group substituted by 1 to 3 aryl groups, a methyl group substituted by 1 to 3 aryl groups, with aryl rings being substituted by a lower alkyl, lower alkoxy, halogen or cyano, a silyl group, a phosphoroamidite group, or —P(O) $(R_9)R_{10}$
wherein
$R_9$ and $R_{10}$ are the same or different and each represents a hydroxyl group, a hydroxyl group protected with a protective group for synthesis of nucleic acid, a mercapto group, a mercapto group protected for synthesis of nucleic acid, an amino group, an alkoxy group having 1 to 5 carbon atoms, an alkylthio group having 1 to 5 carbon atoms, a cyanoalkoxy group having 1 to 6 carbon atoms, or an amino group substituted by an alkyl group having 1 to 5 carbon atoms.

14. The compound or salt thereof according to claim 10, wherein $R_6$ represents a hydrogen atom, an acetyl group, a benzoyl group, a benzyl group, a p-methoxybenzyl group, a tert-butyldiphenylsilyl group, —P(OC$_2$H$_4$CN) (N(i-Pr)2), —P(OCH$_3$) (N(i-Pr)$_2$), or a 2-chlorophenyl- or 4-chlorophenylphosphate group.

15. The compound or salt thereof according to claim 10, wherein B represents a 6-aminopurin-9-yl group also known as an adeninyl group, a 6-aminopurin-9-yl group having an amino group protected with a protective group for synthesis of nucleic acid, a 2,6-diaminopurin-9-yl group, a 2-amino-6-chloropurin-9-yl group, a 2-amino-6-chloropurin-9-yl group having an amino group protected with a protective group for synthesis of nucleic acid, a 2amino-6-fluoropurin-9-yl group, a 2-amino-6-fluoropurin-9-yl group having an amino group protected with a protective group for synthesis of nucleic acid, a 2-amino-6-bromopurin-9-yl group, a 2-amino-6bromopurin-9-yl group having an amino group protected with a protective group for synthesis of nucleic acid, a 2-amino-6-hydroxypurin-9-yl group also known as a guaninyl group, a 2-amino-6-hydroxypurin-9-yl group having an amino group protected with a protective group for synthesis of nucleic acid, a 6amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group also known as a cytosinyl group, a 2-oxo-4-amino-1,2-dihydropyrimidin-1-yl group having an amino group protected with a protective group for synthesis of nucleic acid, a 2-oxo-4-amino-5-fluoro-1,2-dihydropyrimidin-1-yl group, a 2-oxo-4-amino-5-fluoro-1,2-dihydropyrimidin-1-yl group having an amino group protected with a protective group for synthesis of nucleic acid, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2dihydropyrimidinlyl group, a 2oxo-4-hydroxy-1,2-dihydropyrimidin1-yl group also known as a uracinyl group, a 2-oxo-4-hydroxy-5-methyl-1,2-dihydropyrimidin-1-yl group also known as a thyminyl group, a 4-amino-5-methyl-2-oxo-1,2-dihydropyrimidin-1-yl group also known as a 5-methylcytosinyl group, or a 4-amino-5-methyl-2-oxo-1,2-dihydropyrimidin-1-yl group having an amino group protected with a protective group for synthesis of nucleic acid.

16. The compound or salt thereof according to claim 10, wherein
B represents a 2-oxo-pyrimidin-1-yl group or a 2-oxo-pyrimidin-1-yl group which has a substituent selected from:
a hydroxyl group, a hydroxyl group protected with a protective group for synthesis of nucleic acid, an alkoxy group having 1 to 5 carbon atoms, a mercapto group, a mercapto group protected with a protective group for synthesis of nucleic acid, an alkylthio group having 1 to 5 carbon atoms, an amino group, an amino group protected with a protective group for synthesis of nucleic acid, an amino group substituted by an alkyl group having 1 to 5 carbon atoms, an alkyl group having 1 to 5 carbon atoms, and a halogen atom.

17. The compound or salt thereof according to claim 10, wherein
B represents a 2-oxo-4-amino-1,2-dihydropyrimidin-1-yl group also known as cytosinyl group, a 2-oxo-4-amino-1,2-dihydropyrimidin-1-yl group having an amino group protected with a protective group for synthesis of nucleic acid, a 2-oxo-4-amino-5-fluoro-1,2-dihydropyrimidin-1-yl group, a 2oxo-4-amino-5-fluoro-1,2-dihydropyrimidin-1-yl group having an amino group protected with a protective group for synthesis of nucleic acid, a 4-amino-2-oxo--5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group also known as uracinyl group, a 2-oxo-4-hydroxy-5-methyl-1,2-dihydropyrimidin-1-yl group also known as thyminyl group, a 4-amino-5-methyl-2-oxo-1,2-dihydropyrimidin-1-yl group also known as 5methylcytosinyl group, or a 4-amino-5-methyl-2-oxo-1,2-dihydropyrimidin-1-yl group having an amino group protected with a protective group for synthesis of nucleic acid,
$R_5$ and $R_6$ are identical or different, and each represent a hydrogen atom, a protective group for a hydroxyl group for synthesis of nucleic acid, an alkyl group, an alkenyl group, a cycloalkyl group, an aryl group, an aralkyl group, an acyl group, a silyl group, —P(O) $(R_9)R_{10}$, or —P($R_9$)$R_{10}$ wherein
$R_9$ and $R_{10}$ are identical or different, and each represent a hydroxyl group, a hydroxyl group protected with a protective group for synthesis of nucleic acid, a mercapto group, a mercapto group protected with a protective group for synthesis of nucleic acid, an amino group, an alkoxy group having 1 to 5 carbon atoms, an alkylthio group having 1 to 5 carbon atoms, a cyanoalkoxy group having 1 to 6 carbon atoms, or an amino group substituted by an alkyl group having 1 to 5 carbon atoms.

18. The compound or salt thereof according to claim 10, wherein
B represents a 2oxo-pyrimidin-1-yl group which has (a) substituent(s) selected from:
a hydroxyl group, a hydroxyl group protected with a protective group for synthesis of nucleic acid, an amino group, an amino group protected with a protective group for synthesis of nucleic acid, and a methyl group.

19. The compound or salt thereof according to claim 10, wherein

B represents a 2-oxo-4amino-1,2-dihydropyrimidin-1-yl group also known as cytosinyl group, a 2oxo-4-amino-1,2-dihydropyrimidin-1-yl group having an amino group protected with a protective group for synthesis of nucleic acid, a 2-oxo-4-hydroxy-5-methyl-1,2-dihydropyrimidin-1-yl group also known as thyminyl group, $R_5$ and $R_6$ are identical or different, and each represent a hydrogen atom, a protective group for a hydroxyl group for synthesis of nucleic acid, an aralkyl group, an acyl group, or a silyl group.

20. An oligonucleotide analogue containing one or more units having one or both of a structure represented by the following general formula (3) and a structure represented by the following general formula (4), or a pharmacologically acceptable salt of said oligonucleotide analogue, provided that if said oligonucleotide analogue or salt thereof contains two or more units having one or both of said structures, B is identical or different among said structures

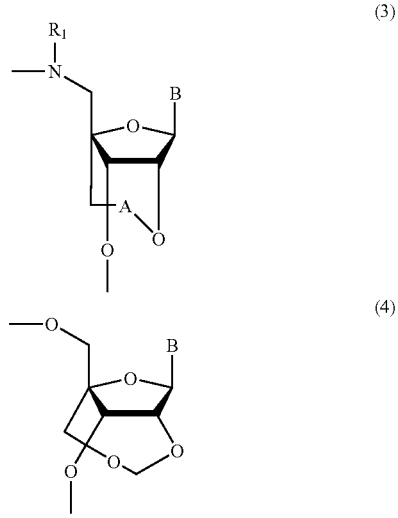

wherein

A represents a direct bond or —O—(CH2)— (wherein the oxygen atom is linked to a metlylene group at the 4'-position), B represents a purin9-yl group, a 2-oxo-pyrimidin-1-yl group, or a purin-9-yl group or a 2-oxo-pyrimidin-1-yl group which has a substituent selected from the following α group:

α group: a hydroxyl group, a hydroxyl group protected with a protective group fo synthesis of nucleic acid, an alkoxy group having 1 to 5 carbon atoms, a mercapto group, a mercapto group protected with a protective group for synthesis of nucleic acid, an alkylthio group having 1 to 5 carbon atoms, an amino group, an amino group protected with a protective group for synthesis of nucleic acid, an amino group substituted by an alkyl group having 1 to 5 carbon atoms, an alkyl group having 1 to 5 carbon atoms, and a halogen atom, and $R_1$ represents a hydrogen atom, an alkyl group, an alkenyl group, a cycloalkyl group, an aryl group, an aralkyl group, an acyl group, a silyl group, or —P($R_7$)$R_8$ wherein $R_7$ and $R_8$ are identical or different, and each represents a hydroxyl group, a hydroxyl group protected with a protective group for synthesis of nucleic acid, a mercapto group, a mercapto group protected with a protective group for synthesis of nucleic acid, an amino group, an alkoxy group having 1 to 5 carbon atoms, an alkylthio group having 1 to 5 carbon atoms, a cyanoalkoxy group having 1 to 6 carbon atoms, or an amino group substituted by an alkyl group having 1 to 5 carbon atoms.

21. The oligonucleotide analogue or pharmacologically acceptable salt thereof according to claim 12, containing one or more units having said structure represented by the general formula (3) (the definitions in the formula are the same as in claim 12.

22. The oligonucleotide analogue or pharmacologically acceptable salt thereof according to claim 13, wherein $R_1$ represents a hydrogen atom, an aliphatic acyl group, an aromatic acyl group, a methyl group substituted by 1 to 3 aryl groups, a methyl group substituted by 1 to 3 aryl groups, with aryl rings being substituted by a lower alkyl, lower alkoxy, halogen or cyano, or a silyl group.

23. The oligonucleotide analogue or pharmacologically acceptable salt thereof according to claim 21, wherein B represents a 2-oxo-pyrimidin-1-yl group or a 2-oxo-pyrimidin-1-yl group which has a substituent selected from: a hydroxyl group, a hydroxyl group protected with a protective group for synthesis of nucleic acid, an alkoxy group having 1 to 5 carbon atoms, a mercapto group, a mercapto group protected with a protective group for synthesis of nucleic acid, an alkylthio group having 1 to 5 carbon atoms, an amino group, an amino group protected with a protective group for synthesis of nucleic acid, an amino group substituted by an alkyl group having 1 to 5 carbon atoms, an alkyl group having 1 to 5 carbon atoms, and a halogen atom.

24. The oligonucleotide analogue or pharmacologically acceptable salt thereof according to claim 21, wherein B represents a 2-oxo-pyrimidin-1-yl group which has (a) substituent(s) selected from: a hydroxyl group, a hydroxyl group protected with a protective group for synthesis of nucleic acid, and a methyl group.

25. The oligonucleotide analogue or pharmacologically acceptable salt thereof according to claim 21, wherein B represents a 2-oxo-4-amino-1,2-dihydropyrimidin-1-yl group also known as cytosinyl group, a 2-oxo-4-amino-1,2-dihydropyrimidin-1-yl group having an amino group protected with a protective group for synthesis of nucleic acid, a 2-oxo-4-amino-5-fluoro-1,2-dihydropyrimidin-1-yl group, a 2-oxo-4-amino-5-fluoro-1,2-dihydropyrimidin-1-yl group having an amino group protected with a protective group for synthesis of nucleic acid, a 4amino-2-oxo-5-chloro-1,2-dihydropyrimidin-1-yl group, a 2oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group also known as uracinyl group, a 2-oxo-4-hydroxy-5-methyl-1,2-dihydropyrimidin-1-yl group also known as thyminyl group, a 4-amino-5-methyl-2-oxo-1,2-dihydropyrimidin-1-yl group also known as 5-methylcytosinyl group, or a 4-amino-5-methyl-2-oxo-1,2-dihydropyrimidin-1-yl group having an amino group protected with a protective group for synthesis of nucleic acid, and $R_1$ represents a hydrogen atom, a protective group for an amino group for synthesis of nucleic acid, an alkyl group, an alkenyl group, a cycloalkyl group, an aryl group, an aralkyl group, an acyl group, a silyl group, —P(O) ($R_7$)$R_8$, or —P($R_7$)$R_8$ wherein $R_7$ and $R_3$ are identical or different, and each represent a hydroxyl group, a hydroxyl group protected with a protective group for synthesis of nucleic acid, a mercapto group, a mercapto group protected with a protective group for synthesis of nucleic acid, an amino group, an alkoxy group having 1 to 5 carbon atoms, an alkylthio group having 1 to 5 carbon atoms, a cyanoalkoxy group having 1 to 6 carbon atoms, or an amino group substituted by an alkyl group having 1 to 5 carbon atoms.

26. The oligonucleotide analogue or pharmacologically acceptable salt thereof according to claim 21, wherein
B represents a 2-oxo-4-hydroxy-5-methyl,2-dihydropyrimidin-1-yl group also known as thyminyl group, and $R_1$ represents a hydrogen atom.

27. The oligonucleotide analogue or pharmacologically acceptable salt thereof according to claim 12, containing one or more units having said structure represented by the general formula (4) (the definitions in the formula are the same as in claim 12).

28. The oligonucleotide analogue or pharmacologically acceptable salt thereof according to claim 27, wherein
B represents a 2-oxo-pyrimidin-1-yl group or a 2-oxo-pyrimidin-1-yl group which has a substituent selected from: a hydroxyl group, a hydroxyl group protected with a protective group for synthesis of nucleic acid, an alkoxy group having 1 to 5 carbon atoms, a mercapto group, a mercapto group protected with a protective group for synthesis of nucleic acid, an alkylthio group having 1 to 5 carbon atoms, an amino group, an amino group protected with a protective group for synthesis of nucleic acid, an amino group substituted by an alkyl group having 1 to 5 carbon atoms, an alkyl group having 1 to 5 carbon atoms, and a halogen atom.

29. The oligonucleotide analogue or pharmacologically acceptable salt thereof according to claim 27, wherein
B represents a 2-oxo-4-amino-1,2-dihydropyrimidin-1-yl group also known as cytosinyl group, a 2-oxo-4-amino-1,2-dihydropyrimidin-1-yl group having an amino group protected with a protective group for synthesis of nucleic acid, a 2-oxo-4-amino-5-fluoro-1,2-dihydropyrimidin-1-yl group a 2-oxo-4-amino-5-fluoro-1,2-dihydropyrimidin-1-yl group having an amino group protected with a protective group for synthesis of nucleic acid, a 4amino-2-oxo-5-chloro-1,2-dihydropyrimidin-1-yl group, a 2oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group also known as uracinyl group, a 2-oxo-4-hydroxy-5-methyl-1,2-dihydropyrimidin-1-yl group also known as thyminyl group, a 4-amino-5-methyl-2oxo-1,2-dihydropyrimidin-1-yl group also known as 5-methylcytosinyl group, or a 4-amino-5-methyl-2-oxo-1,2-dihydropyrimidin-1-yl group having an amino group protected with a protective group for synthesis of nucleic acid.

30. The oligonucleotide analogue or pharmacologically acceptable salt thereof according to claim 27, wherein
B represents a 2-oxo-pyrimidin-1-yl group which has (a) substituent(s) selected from: a hydroxyl group, a hydroxyl group protected with a protective group for synthesis of nucleic acid, an amino group protected with a protective group for synthesis of nucleic acid, and a methyl group.

31. The oligonucleotide analogue or pharmacologically acceptable salt thereof according to claim 27, wherein
B represents a 2oxo-4-amino-1,2-dihydropyrimidin-1-yl group also known as cytosinyl group, a 2-oxo-4-amino-1,2-dihydropyrimidin-1-yl group having an amino group protected with a protective group for synthesis of nucleic acid, a 2-oxo-4-hydroxy-5-methyl-1,2-dihydropyrimidin-1-yl group also known as thyminyl group.

32. The oligonucleotide analogue or pharmacologically acceptable salt thereof according to claim 20, wherein B represents a 6-aminopurin-9-yl group also known as a adeninyl group, a 6-aminopurin-9-yl group having an amino group protected with a protective group for synthesis of nucleic acid, a 2,6diaminopurin-9-yl group, a 2-amino-6-chloropurin-9-yl group, a 2-amino-6-chloropurin-9-yl group having an amino group protected with a protective group for synthesis of nucleic acid, a 2-amino-6-fluoropurin-9-yl group, a 2amino-6-fluoropurin-9-yl group having an amino group protected with a protective group for synthesis of nucleic acid, a 2-amino-6-bromopurin-9-yl group, a 2-amino-6-bromopurin-9-yl group having an amino group protected with a protective group for synthesis of nucleic acid, a 2-amino-6-hydroxypurin-9-yl group also known as a guaninyl group, a 2-amino-6-hydroxypurin-9-yl group having an amino group protected with a protective group for synthesis of nucleic acid, a 5amino-methoxypurin9-yl group, a 6-amino-2-chloropurin-9-yl group, a 6amino-2-fluoropurin-9-yl group, a 2,6-dimethoxypurin-9-yl group, a 2,6dichloropurin-9-yl group, a 6-mercaptopurin-9-yl group, a 2-oxo-4-amino-1,2-dihydropyrimidin-1-yl group also known as a cytosinyl group, a 2-oxo-4-amino-1,2-dihydropyrimidin-1-yl group having an amino group protected with a protective group for synthesis of nucleic acid, a 2-oxo-4-amino-5-fluoro-1,2-dihydropyrimidin-1-yl group, a 2-oxo-4-amino-5-fluoro-1,2-dihydropyrirnidin-1-yl group having an amino group protected with a protective group for synthesis of nucleic acid, a 4-amino-2-oxo-5-chloro-1,2-dihydropyrimidin-1-yl group, a 2-oxo-4methoxy-1,2-dihydropyrimidin-1-yl group, a 2oxo-4-mercapto-1,2-dihydropyrimidin-1-yl group, a 2-oxo-4-hydroxy-1,2-dihydropyrimidin-1-yl group also known as a uracinyl group, a 2-oxo-4-hydroxy-5-methyl-1,2-dihydropyrimidin-1-yl group also known as a thyminyl group, a 4-amino-5-methyl-2-oxo-1,2-dihydropyrimidin-1-yl group also known as a 5-methylcytosinyl group, or a 4-amino-5-methyl-2-oxo-1,2-dihydropyrimidin-1-yl group having an amino group protected with a protective group for synthesis of nucleic acid.

33. The oligonucleotide analogue or pharmacologically acceptable salt thereof according to claim 20, wherein
B represents a 2-oxo-pyrimidin-1-yl group or a 2-oxo-pyrimidin-1-yl group which has a substituent selected from: a hydroxyl group, a hydroxyl group protected with a protective group for synthesis of nucleic acid, an alkoxy group having 1 to 5 carbon atoms, a mercapto group, a mercapto group protected with a protective group for synthesis of nucleic acid, an alkylthio group having 1 to 5 carbon atoms, an amino group, an amino group protected with a protective group for synthesis of nucleic acid, an amino group substituted by an alkyl group having 1 to 5 carbon atoms, an alkyl group having 1 to 5 carbon atoms, and a halogen atom.

34. The oligonucleotide analogue or pharmacologically acceptable salt thereof according to claim 20, wherein
B represents a 2-oxo-pyrimidin-1-yl group which has (a) substituent(s) selected from: a hydroxyl group, a hydroxyl group protected with a protective group for synthesis of nucleic acid, an amino group, an amino group protected with a protective group for synthesis of nucleic acid, and a methyl group.

* * * * *

UNITED STATES PATENT AND TRADEMARK OFFICE
CERTIFICATE OF CORRECTION

| | | |
|---|---|---|
| PATENT NO. | : 7,615,619 B2 | Page 1 of 1 |
| APPLICATION NO. | : 10/504165 | |
| DATED | : November 10, 2009 | |
| INVENTOR(S) | : Takeshi Imanishi | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 462 days.

Signed and Sealed this

Nineteenth Day of October, 2010

David J. Kappos
*Director of the United States Patent and Trademark Office*

SEQUENCE LISTING

<160> NUMBER OF SEQ ID NOS: 16

<210> SEQ ID NO 1
<211> LENGTH: 10
<212> TYPE: DNA
<213> ORGANISM: Artificial
<220> FEATURE:
<223> OTHER INFORMATION: Antisense
<220> FEATURE:
<221> NAME/KEY: misc_feature
<222> LOCATION: (6)..(6)
<223> OTHER INFORMATION: n is a, c, g, or t

<400> SEQUENCE: 1 tttttntttt                                                                10

<210> SEQ ID NO 2

```
<211> LENGTH: 10
<212> TYPE: DNA
<213> ORGANISM: Artificial
<220> FEATURE:
<223> OTHER INFORMATION: Antisense
<220> FEATURE:
<221> NAME/KEY: misc_feature
<222> LOCATION: (2)..(9)
<223> OTHER INFORMATION: n is a, c, g, or t

<400> SEQUENCE: 2 tnnnnnnnnt                                                              10

<210> SEQ ID NO 3
<211> LENGTH: 9
<212> TYPE: DNA
<213> ORGANISM: Artificial
<220> FEATURE:
<223> OTHER INFORMATION: Antisense
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 3 tttntntnt                                                                9

<210> SEQ ID NO 4
<211> LENGTH: 10
<212> TYPE: DNA
<213> ORGANISM: Artificial
<220> FEATURE:
<223> OTHER INFORMATION: Antisense
<220> FEATURE:
<221> NAME/KEY: misc_feature
<222> LOCATION: (9)..(9)
<223> OTHER INFORMATION: n is a, c, g, or t

<400> SEQUENCE: 4 tttttttnt                                                               10

<210> SEQ ID NO 5
<211> LENGTH: 10
<212> TYPE: DNA
<213> ORGANISM: Artificial
<220> FEATURE:
<223> OTHER INFORMATION: Antisense
<220> FEATURE:
<221> NAME/KEY: misc_feature
<222> LOCATION: (2)..(2)
<223> OTHER INFORMATION: n is a, c, g, or t

<400> SEQUENCE: 5 tnttttttttt                                                             10

<210> SEQ ID NO 6
<211> LENGTH: 16
<212> TYPE: DNA
<213> ORGANISM: Artificial
<220> FEATURE:
<223> OTHER INFORMATION: Antisense
<220> FEATURE:
<221> NAME/KEY: misc_feature
```

-continued

```
<222> LOCATION: (8)..(8)
<223> OTHER INFORMATION: n is a, c, g, or t

<400> SEQUENCE: 6
tcttcttntt ctctct                                                    16

<210> SEQ ID NO 7
<211> LENGTH: 16
<212> TYPE: DNA
<213> ORGANISM: Artificial
<220> FEATURE:
<223> OTHER INFORMATION: Antisense
<220> FEATURE:
<221> NAME/KEY: misc_feature
<222> LOCATION: (7)..(9)
<223> OTHER INFORMATION: n is a, c, g, or t

<400> SEQUENCE: 7
tcttctnnnt ctctct                                                    16

<210> SEQ ID NO 8
<211> LENGTH: 16
<212> TYPE: DNA
<213> ORGANISM: Artificial
<220> FEATURE:
<223> OTHER INFORMATION: Antisense
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t

<400> SEQUENCE: 8
tcttcntntn ctctct                                                    16

<210> SEQ ID NO 9
<211> LENGTH: 16
<212> TYPE: DNA
<213> ORGANISM: Artificial
<220> FEATURE:
<223> OTHER INFORMATION: Antisense
<220> FEATURE:
<221> NAME/KEY: misc_feature
<222> LOCATION: (6)..(10)
<223> OTHER INFORMATION: n is a, c, g, or t

<400> SEQUENCE: 9
tcttcnnnnn ctctct                                                    16

<210> SEQ ID NO 10
<211> LENGTH: 15
<212> TYPE: DNA
<213> ORGANISM: Artificial
<220> FEATURE:
<223> OTHER INFORMATION: Antisense
<220> FEATURE:
<221> NAME/KEY: misc_feature
<222> LOCATION: (8)..(8)
<223> OTHER INFORMATION: n is a, c, g, or t

<400> SEQUENCE: 10
tttttctntc tctct                                                     15
```

```
<210> SEQ ID NO 11
<211> LENGTH: 12
<212> TYPE: DNA
<213> ORGANISM: Artificial
<220> FEATURE:
<223> OTHER INFORMATION: Antisense

<400> SEQUENCE: 11
tttttttttt tt                                                          12

<210> SEQ ID NO 12
<211> LENGTH: 12
<212> TYPE: DNA
<213> ORGANISM: Artificial
<220> FEATURE:
<223> OTHER INFORMATION: Antisense
<220> FEATURE:
<221> NAME/KEY: misc_feature
<222> LOCATION: (6)..(6)
<223> OTHER INFORMATION: n is a, c, g, or t

<400> SEQUENCE: 12
tttttntttt tt                                                          12

<210> SEQ ID NO 13
<211> LENGTH: 12
<212> TYPE: DNA
<213> ORGANISM: Artificial
<220> FEATURE:
<223> OTHER INFORMATION: Antisense
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 13
tttttntntt tt                                                          12

<210> SEQ ID NO 14
<211> LENGTH: 12
<212> TYPE: DNA
<213> ORGANISM: Artificial
<220> FEATURE:
<223> OTHER INFORMATION: Antisense
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 14 ntttntntt tt                                                           12

<210> SEQ ID NO 15
<211> LENGTH: 12
<212> TYPE: DNA
<213> ORGANISM: Artificial
<220> FEATURE:
<223> OTHER INFORMATION: Antisense
```

```
<220> FEATURE:
<221> NAME/KEY: misc_feature
<222> LOCATION: (6)..(8)
<223> OTHER INFORMATION: n is a, c, g, or t

<400> SEQUENCE: 15
tttttnnntt tt                                                          12

<210> SEQ ID NO 16
<211> LENGTH: 12
<212> TYPE: DNA
<213> ORGANISM: Artificial
<220> FEATURE:
<223> OTHER INFORMATION: Antisense
<220> FEATURE:
<221> NAME/KEY: misc_feature
<222> LOCATION: (1)..(12)
<223> OTHER INFORMATION: n is a, c, g, or t

<400> SEQUENCE: 16
nnnnnnnnnn nn                                                          12
```